US012806288B2

(12) United States Patent
Junn et al.

(10) Patent No.: US 12,806,288 B2
(45) Date of Patent: Nov. 24, 2026

(54) MicroRNA-7 COMPOSITIONS FOR PROMOTING FUNCTIONAL RECOVERY FOLLOWING SPINAL CORD INJURY AND METHODS OF USE THEREOF

(71) Applicant: Rutgers, The State University of New Jersey, New Brunswick, NJ (US)

(72) Inventors: Eunsung Junn, East Brunswick, NJ (US); Mary M. Mouradian, Princeton, NJ (US); Myung-Sik Yoo, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 906 days.

(21) Appl. No.: 17/759,832

(22) PCT Filed: Feb. 1, 2021

(86) PCT No.: PCT/US2021/016044
§ 371 (c)(1),
(2) Date: Jul. 29, 2022

(87) PCT Pub. No.: WO2021/158476
PCT Pub. Date: Aug. 12, 2021

(65) Prior Publication Data

US 2023/0070049 A1 Mar. 9, 2023

Related U.S. Application Data

(60) Provisional application No. 62/969,338, filed on Feb. 3, 2020.

(51) Int. Cl.
*C12N 15/86* (2006.01)
*A61K 48/00* (2006.01)

(52) U.S. Cl.
CPC ........... *A61K 48/005* (2013.01); *C12N 15/86* (2013.01); *C12N 2310/141* (2013.01); *C12N 2330/51* (2013.01); *C12N 2750/14143* (2013.01)

(58) Field of Classification Search
CPC .................... A61K 48/00; C12N 15/63; C12N 2310/141
See application file for complete search history.

(56) References Cited

U.S. PATENT DOCUMENTS

| | | | | |
|---|---|---|---|---|
| 7,232,806 | B2 | 6/2007 | Tuschl et al. | |
| 9,255,266 | B2 * | 2/2016 | Mouradian et al. | C12N 15/113 435/6 |
| 2004/0219671 | A1 | 11/2004 | McSwiggen et al. | |
| 2005/0185691 | A1 | 8/2005 | Slater | |
| 2008/0166414 | A1 | 7/2008 | Hanes et al. | |
| 2008/0306006 | A1 | 12/2008 | Croce et al. | |
| 2009/0004668 | A1 | 1/2009 | Chen et al. | |
| 2009/0247466 | A1 | 10/2009 | Hagg et al. | |
| 2014/0294943 | A1 | 10/2014 | Juo et al. | |
| 2016/0046936 | A1 | 2/2016 | Li et al. | |
| 2016/0333357 | A1 | 11/2016 | Feinstein et al. | |
| 2017/0304348 | A1 | 10/2017 | Berezikov et al. | |
| 2019/0167762 | A1 | 6/2019 | Dickson et al. | |

FOREIGN PATENT DOCUMENTS

| | | | |
|---|---|---|---|
| JP | 2007534729 | A | 11/2007 |
| JP | 2013046612 | A | 3/2013 |
| JP | 2017510298 | A | 4/2017 |
| JP | 2018505240 | A | 2/2018 |
| WO | 2002044321 | A2 | 6/2002 |
| WO | 2006039253 | A2 | 4/2006 |
| WO | 2007104633 | A1 | 9/2007 |
| WO | 2007135426 | A2 | 11/2007 |
| WO | 2008025073 | A1 | 3/2008 |
| WO | 2011/057171 | A1 | 5/2011 |
| WO | 2014007120 | A1 | 1/2014 |

OTHER PUBLICATIONS

Zhao et al. (2015) "MicroRNA-7: a promising new target in cancer therapy" Cancer cell international, 15:103, 8 pages. (Year: 2015).*
Li et al. (2016) "miR-7a/b attenuates post-myocardial infarction remodeling and protects H9c2 cardiomyoblast against hypoxia-induced apoptosis involving Sp1 and PARP-1" Sci Rep 6, 29082, 11 pages. (Year: 2016).*
Zeng et al. (2019) "Lentivirus-mediated downregulation of α-synuclein reduces neuroinflammation and promotes functional recovery in rats with spinal cord injury" Journal of neuroinflammation, 16, 1-19. (Year: 2019).*
Ding et al. (Jan. 13, 2020) "MIR-7a ameliorates spinal cord injury by inhibiting neuronal apoptosis and oxidative stress" European Review for Medical & Pharmacological Sciences, 24(1), pp. 11-17. (Year: 2020).*
Challagundla et al. (2015) "AAV-mediated expression of BAG1 and ROCK2-shRNA promote neuronal survival and axonal sprouting in a rat model of rubrospinal tract injury" Journal of Neurochemistry, 134(2), 261-275. (Year: 2015).*
Koprich et al. (2010) Expression of human A53T alpha-synuclein in the rat substantia nigra using a novel AAV1/2 vector produces a rapidly evolving pathology with protein aggregation, . . . [continued on citation V] (Year: 2010).*
[Continued from citation U] . . . dystrophic neurite architecture and nigrostriatal degeneration with potential to model the pathology of Parkinson's disease Molecular neurodegeneration, 5, 1-12. (Year: 2010).*

(Continued)

*Primary Examiner* — James Joseph Graber
(74) *Attorney, Agent, or Firm* — FOX ROTHSCHILD LLP

(57) ABSTRACT

Compositions, recombinant viral vectors, recombinant viruses, and nanoparticles for treating a subject having a spinal cord injury include a therapeutically effective amount of a nucleic acid sequence encoding pre-microRNA-7 (pre-miR-7). Methods of using these compositions, recombinant viral vectors, recombinant viruses, and nanoparticles are also described herein. These compositions, recombinant viral vectors, recombinant viruses, and nanoparticles and methods of use provide novel therapies for SCI based on the discovery that miR-7 expression provides neuroprotection and recovery of locomotor function in subjects having SCI.

8 Claims, 11 Drawing Sheets

Specification includes a Sequence Listing.

(56) References Cited

OTHER PUBLICATIONS

Sakai et al. (2013) "miR-7a alleviates the maintenance of neuropathic pain through regulation of neuronal excitability" Brain, 136(9), 2738-2750. (Year: 2013).*
Hu et al. (2019) "Silencing of IncRNA PKIA-AS1 attenuates spinal nerve ligation-induced neuropathic pain through epigenetic downregulation of CDK6 expression" Frontiers in cellular neuroscience, vol. 13, Article 50, 12 pages. (Year: 2019).*
Jan et al. (2019) "Gene transfer in rodent nervous tissue following hindlimb intramuscular delivery of recombinant adeno-associated virus serotypes AAV2/6, AAV2/8, and AAV2/9" Neuroscience Insights, vol. 14, 12 pages. (Year: 2019).*
Yoo et al. (2021) "MicroRNA-7 promotes motor function recovery following spinal cord injury in mice" Biochemical and biophysical research communications, 573, 80-85. (Year: 2021).*
Chakrabarti, et al: "miR-7-1 Potentiated Estrogen Receptor Agonists for Functional Neuroprotection in VSC4.1 Motoneurons", Neuroscience, Jan. 3, 2014, vol. 256, pp. 322-333, doi: 10.1016/j.neuroscience.2013.10.027.
Yoo et al: "MicroRNA-7 promotes motor function recovery following spinal cord injury in mice", Biochemical and Biophysical Research Communications, 2021, 573. pp. 80-85.
Agrawal, et al: "Antisense therapeutics: is it as simple as complementary base recognition?", Feb. 2000, Molecular Medicine Today, vol. 6, pp. 72-81.
Anonymous: "Scientific Program of the 22nd Conference of the Hellenic Society for Neuroscience"; Oct. 16-19, 2008.
Bartus, et al: "Safety/feasibility of targeting the substantia nigra with AAV2-neurturin in Parkinson patients", Neurology, 2013;80:1698-1701.
Bushati, et al: "MicroRNAs in Neurodegeneration"; 2008, Current Opinion in Neurobiology; vol. 18, pp. 292-296.
Chirila, et al: "The Use of Synthetic Polymers for Delivery of Therapeutic Antisense Oligodeoxynucleotides"; Biomaterials, 2002, vol. 23, pp. 321-342.
Christine, et al: "Safety and tolerability of putaminal AADC gene therapy for Parkinson disease", Neurology, 2009;73:1662-1669.
Crooke, S.T.: "Progress in Antisense Technology"; Annu. Rev. Medicine, 2004, vol. 55, pp. 61-95.
Doench, et al: "Specificity of MicroRNA Target Selection in Translational Repression"; 2004, Genes & Development, vol. 18, No. 5, pp. 504-511.
Doxakis, E.: "Post-Transcriptional Regulation of Alpha-Synuclein Expression by MIR-7 and MIR-53"; Apr. 23, 2010, The Journal of Biological Chemistry, vol. 285, No. 17, pp. 1-14.
Eberling, et al: "Results from a phase I safety trial of hAADC gene therapy for Parkinson disease", Neurology, 2008; 70, pp. 1980-1983.
Holen, et al: "Positional Effects of Short Interfering RNAs Targeting the Human Coagulation Trigger Tissue Factor"; 2002, Nucleic Acids Research, vol. 30, No. 8, pp. 1757-1766.
Jang, et al: "Gene Delivery from Polymer Scaffolds for Tissue Engineering"; Expert Rev. Medical Devices, 2004, vol. 1, No. 1, pp. 127-138.
Junn, et al: "Repression of Alpha-Synuclein Expression and Toxicity by MicroRNA-7"; Aug. 4, 2009, Proceedings of the National Academy of Sciences of the United States of America, vol. 106, No. 31, pp. 13052-13057.
Kaplitt, et al: "Safety and tolerability of gene therapy with an adeno-associated virus (AAV) borne GAD gene for Parkinson's disease: an open label, phase I trial", Lancet, 2007; 369: 2097-105.
Lewitt, et al: "AAV2-GAD gene therapy for advanced Parkinson's disease: a double-blind, sham-surgery controlled, randomised trial", Lancet Neurol 2011; 10: 309-19.
Marks Jr., et al: "Safety and tolerability of intraputaminal delivery of CERE-120 (adeno-associated virus serotype 2-neurturin) to patients with idiopathic Parkinson's disease: an open-label, phase I trial", Lancet Neurol 2008; 7: 400-08.
Marks Jr., et al: "Gene delivery of AAV2-neurturin for Parkinson's disease: a double-blind, randomised, controlled trial", Lancet Neurol, 2010; 9: 1164-72.
Mittermeyer, et al: "Long-Term Evaluation of a Phase 1 Study of AADC Gene Therapy for Parkinson's Disease", Human Gene Therapy, 23:377-381 (Apr. 2012).
Muramatsu, et al: "A Phase I Study of Aromatic I-Amino Acid Decarboxylase Gene Therapy for Parkinson's Disease", Molecular Therapy, vol. 18, No. 9, pp. 1731-1735, Sep. 2010.
Nelson, et al: "The mRNA of Alpha-Synuclein is a Putative MicroRNA (MIRNA) Target"; Jan. 1, 2003, Annual Meeting of the Society of Neuroscience, (Abstract Only).
Opalinska, et al: "Nucleic-Acid Therapeutics: Basic Principles and Recent Applications"; Jul. 2002, Nature Reviews; vol. 1, pp. 503-514.
Palfi, et al: "Long-term safety and tolerability of ProSavin, a lentiviral vector-based gene therapy for Parkinson's disease: a dose escalation, open-label, phase 1/2 trial", Lancet 2014; 383: 1138-46.
Paroo, et al: "Challenges for RNAi in Vivo"; Aug. 2004, Trends in Biotechnology; vol. 22, No. 8, pp. 390-394.
Peracchi, A: "Prospects for Antiviral Ribozymes and Deoxyribozymes"; 2004, Rev. Med. Virol, vol. 14, pp. 47-64.
Rothschild, S.I.: "microRNA therapies in cancer", Rothschild Molecular and Cellular Therapies, 2014, 2:7.
Tagliafierro, et al: "Genetic Analysis of a-Synuclein 3' Untranslated Region and its Corresponding microRNAs in relation to Parkinson's Disease Compared to Demential with Lewy Bodies", Alzheimer's & Dementia, 2017, vol. 13, pp. 1237-1250.
Valles, et al: "Qualitative Imaging of Adeno-Associated Virus Serotype 2-Human Aromatic L-Amino Acid Decarboxylase Gene Therapy in a Phase I Study for the Treatment of Parkinson Disease", Neurosurgery, 67:1377-1385, 2010.
Vasudevan, et al: "Switching from Repression to Activation: MicroRNAs Can Up-Regulate Translation"; Dec. 21, 2007, Science, vol. 318, pp. 1931-1934.
Zeng, et al: "MicroRNA-210 overexpression induces angiogenesis and neurogenesis in the normal adult mouse brain", Gene Therapy, (2014) 21, 37-43.
Horsham et al: "MicroRNA-7: A miRNA with expanding roles in development and disease", International Journal of Biochemistry and Cell Biology, Elsevier, Amsterdam, NL, Nov. 2015, vol. 69, pp. 215-224, XP029333512, ISSN: 1357-2725, DOI: 10.1016/J.BIOCEL.2015.11.001.
Ning et al: "microRNAs in Spinal Cord Injury: Potential Roles and Therapeutic Implications", International Journal of Biological Sciences, Jan. 1, 2014, vol. 10, No. 9, pp. 997-1006, XP093086665, ISSN: 1449-2288, DOI: 10.7150/ijbs.905.
Ray et al: "Future directions for using estrogen receptor agonists in the treatment of acute and chronic spinal cord injury", Neural Regeneration Research, Jan. 1, 2016, vol. 11, No. 9, pp. 1418-1419, XP093086680, CN ISSN: 1673-5374, DOI: 10.4103/1673-5374.191212.
Zhao et al: "MicroRNA-7: expression and function in brain physiological and pathological processes", Cell & Bioscience, Jun. 10, 2020, vol. 10, No. 1, pp. 1-12, XP093086809, DOI: 10.1186/s13578-020-00436-w. Retrieved from the Internet: <URL:https://link.springer.com/article/10.1186/s13578-020-00436-w/ fulltext.html>.
Zhou et al: "MiR-7 inhibited peripheral nerve injury repair by affecting neural stem cells migration and proliferation through cdc42", Molecular Pain, Jan. 1, 2018, vol. 14, XP093089033, GB ISSN: 1744-8069, DOI: 10.1177/1744806918766793. Retrieved from the Internet: <URL:https://www.ncbi.nlm.nih.gov/pmc/articles/PMC5912295/pdf/ 10.1177 _ 1744806918766793.pdf>.

* cited by examiner

3A

3B

3C

MicroRNA-7 COMPOSITIONS FOR PROMOTING FUNCTIONAL RECOVERY FOLLOWING SPINAL CORD INJURY AND METHODS OF USE THEREOF

CROSS REFERENCE TO RELATED APPLICATION

This application claims priority to U.S. Provisional Application No. 62/969,338 filed on Feb. 3, 2020, which is incorporated by reference herein in its entirety.

FEDERALLY SPONSORED RESEARCH

This invention was made with government support under grant no. NS070898 awarded by the National Institutes of Health. The government has certain rights in the invention.

CROSS-REFERENCE TO A SEQUENCE LISTING

This application includes a "Sequence Listing" which is provided as an electronic document having the file name "096738.00687_ST25.txt" (569 bytes, created Jan. 25, 2021), which is herein incorporated by reference in its entirety.

FIELD OF THE INVENTION

The invention relates generally to the fields of medicine, molecular biology, and gene therapy. In particular, the invention relates to compositions, vectors, viruses, nanoparticles, kits and methods for delivering a microRNA for treating spinal cord injury in a subject.

BACKGROUND

Spinal cord injury (SCI) is damage to the spinal cord including nerves within the bony protection due to trauma or disease. SCI could result in loss of muscle function, sensation, or autonomic function in the parts of the body served by the spinal cord below the level of the injury. These changes in the functionality could be temporary or permanent depending on the type, size and site/location of injury. According to the National Spinal Cord Injury Association, as many as 450,000 people in the United States are living with a SCI. Every year, an estimated 17,000 new SCIs occur in the U.S and as per the Centers for Diseases Control and Prevention (CDC), SCI costs the nation an estimated $9.7 billion each year. There is a great need to find a treatment for SCI.

SUMMARY

Described herein are compositions, vectors, viruses, nanoparticles, kits and methods for promoting functional recovery (e.g., improving locomotor function) in a subject having a SCI. The compositions, vectors, viruses, nanoparticles, kits and methods all include a nucleic acid sequence encoding pre-miR-7. In the experiments described below, it was shown in a SCI mouse model that mice transduced with a recombinant Adeno-Associated Virus (rAAV) vector encoding pre-miR-7 (AAV1-miR-7) had improved locomotor recovery as compared to mice transduced with a control vector (AAV1-miR-SC (scrambled)). The results demonstrated that many cellular responses are accompanied by the miR-7-mediated motor functional recovery such as attenuation of neuroinflammatory responses, increase of neuronal survival and axon regeneration, and protection of oligodendrocytes, and that miR-7 targets several neuroprotective genes and pathways. These results suggest that miR-7 expression through AAV1-miR-7 is providing neuroprotection and recovery of locomotor function and thus miR-7 can be delivered in a novel gene therapy to treat SCI. In some other embodiments, a lentiviral vector that includes a nucleic acid sequence encoding pre-miR-7 is used in the methods.

Accordingly, described herein is a gene therapy vector including a polynucleotide sequence including a nucleic acid sequence encoding pre-microRNA-7 (pre-miR-7). In a typical embodiment the nucleic acid sequence encoding pre-miR-7 is the sequence of SEQ ID NO:1 (5'UUGGAUGUUGGCCUAGUUCUGUGUGGAAGACUAGUGAUUUUGUUGUUUUUAG AUAACUAAAUCGACAACAAAUCACAGUCUGCCAUAUGGCACAGGCCAUGCCUCUA CAG-3'). The gene therapy vector can be a recombinant viral vector, e.g., a recombinant Adeno-Associated Virus (rAAV) vector, or a recombinant lentiviral vector. In some embodiments, the rAAV vector is serotype 2.

Further described herein is a composition including a recombinant virus including a recombinant viral vector including a polynucleotide sequence including a nucleic acid sequence encoding pre-miR-7 in a therapeutically effective amount for improving locomotor function in a subject having a SCI, and a pharmaceutically acceptable carrier. In some embodiments, the recombinant viral vector is a recombinant lentiviral vector.

Yet further described herein is a composition including a rAAV including a rAAV vector including a polynucleotide sequence including a nucleic acid sequence encoding pre-miR-7 in a therapeutically effective amount for improving locomotor function in a subject having a SCI, and a pharmaceutically acceptable carrier. In the composition, the rAAV can include, for example, serotype 1 or 9 capsid proteins and the rAAV vector can be, for example, serotype 2. The rAAV vector can be any suitable serotype. The rAAV can include capsid proteins from any suitable serotype, e.g., an AAV serotype or AAV variant such as: AAV1, AAV2, AAV3, AAV4, AAV5, AAV6, AAV7, AAV8, AAV9, AAV10, AAV 11, AAV12, AAV13, AAVrh10, AAV-PHP.5, AAV-PHP.B, AAV-PHP.eB, AAV-retro, AAV9-retro, or a hybrid thereof.

Still further described herein is a composition including a nanoparticle complexed with polyethylene glycol (PEG) and a nucleic acid sequence encoding pre-miR-7. In some embodiments, the nanoparticle is a gold nanoparticle.

Also described herein is a method of promoting functional recovery in a subject (e.g., a human) following SCI. The method includes administering to the subject having a SCI an effective amount of a composition that includes a nanoparticle complexed with PEG and a nucleic acid sequence encoding pre-miR-7. In some embodiments of the method, the nanoparticle is a gold nanoparticle. In a typical method, the subject is a human and the nanoparticle is a gold nanoparticle.

Further described herein is a method of promoting functional recovery in a subject (e.g., a human) following SCI. The method includes administering to the subject having a SCI an effective amount of a recombinant virus including a recombinant viral vector including a polynucleotide sequence including a nucleic acid sequence encoding pre-miR-7, or an effective amount of a composition including the recombinant virus including a recombinant viral vector including a polynucleotide sequence including a nucleic acid sequence encoding pre-miR-7. Typically, the subject is a mammal, e.g., a human. In some embodiments, other systems such as lentiviral vectors can be used. Lentiviral-based systems can transduce non-dividing as well as dividing cells making them useful for applications targeting, for examples, the non-dividing cells of the CNS. Lentiviral vectors are derived from the human immunodeficiency virus and, like that virus, integrate into the host genome providing the potential for long-term gene expression. Any suitable type of lentivirus or lentivirus system may be used. In a typical embodiment, a third-generation, self-inactivating (SIN) lentiviral vector is used. In other embodiments of the method, the recombinant virus is rAAV. The rAAV can include, for example, serotype 1 or 9 capsid proteins, and the rAAV vector can be, for example, serotype 2. The rAAV vector can be any suitable serotype. The rAAV can include capsid proteins from an AAV serotype or AAV variant such as: AAV1, AAV2, AAV3, AAV4, AAV5, AAV6, AAV7, AAV8, AAV9, AAV10, AAV 11, AAV12, AAV13, AAVrh10, AAV-PHP.5, AAV-PHP.B, AAV-PHP.eB, AAV-retro, AAV9-retro, or a hybrid thereof. Typically, administration of the recombinant virus or the composition including the recombinant virus increases neuronal survival and axon regeneration in the subject, and improves at least one of: locomotor function, bladder function, bowel function, numbness and tingling in the subject. In some methods, the recombinant virus or the composition including the recombinant virus is administered directly to the subject's spinal cord. The recombinant virus or the composition including the recombinant virus can be administered to the subject at at least one (e.g., 1, 2, 3, 4, 5, etc.) of the following time points: within one hour of SCI injury, within 2 hours of SCI injury, within 4 hours of SCI injury, within 6 hours of SCI injury, within 8 hours of SCI injury, within 12 hours of SCI injury, within 24 hours of SCI injury, within 48 hours of SCI injury, within 72 hours of SCI injury, within 7 days of SCI injury, and within one month of SCI injury. In some methods, the subject is administered the recombinant virus or the composition including the recombinant virus via injection. The methods can further include evaluating at least one of: locomotor function, bladder function, bowel function, numbness and tingling in the subject at a time point subsequent to administration of the recombinant virus or the composition including the recombinant virus.

Yet further described herein is a kit for promoting functional recovery in a subject following SCI. The kit includes: a composition including a recombinant virus including a recombinant viral vector including a polynucleotide sequence including a nucleic acid sequence encoding pre-miR-7 in a therapeutically effective amount, and a pharmaceutically acceptable carrier; instructions for use; and packaging. In some kits, the recombinant virus is rAAV and the subject is a human. In other embodiments, the recombinant virus is recombinant lentivirus and the subject is a human.

Still further described herein is a kit for promoting functional recovery in a subject following SCI. The kit includes: a composition including a nanoparticle complexed with PEG and a nucleic acid sequence encoding pre-miR-7, and a pharmaceutically acceptable carrier; instructions for use; and packaging.

As used herein, the terms "pre-miR-7" and "pre-microRNA-7" mean a native human or mouse RNA sequence having the sequence of SEQ ID NO:1 (5'UUGGAUGUUGGCCUAGUUCUGUGUGGAAGACUAGUGAUUUUGUUGUUUUUAG AUAACUAAAUCGACAACAAAUCACAGUCUGCCAUAUGGCACAGGCCAUGCCUCUA CAG-3'). Once in the cytosol of a cell, pre-miR-7 is processed to miR-7 (also referred to as the mature form of miR-7) which is 24 nucleotides in length. The vectors, recombinant viruses and compositions herein contain and deliver pre-miR-7 into cells, where the pre-miR-7 is processed into mature miR-7. As used herein, the term "AAV1-miR-7" means a rAAV expressing pre-miR-7.

As used herein, the phrases "miR-7 overexpression" and "overexpression of miR-7" mean increased levels of miR-7 as compared to normal levels in normal tissues.

By the term "RNA" is meant a molecule comprising at least one ribonucleotide residue.

By the term "gene" is meant a nucleic acid molecule that codes for a particular protein, or in certain cases, a functional or structural RNA (ribonucleic acid) molecule.

As used herein, a "nucleic acid" or a "nucleic acid molecule" means a chain of two or more nucleotides such as RNA and DNA (deoxyribonucleic acid).

As used herein, the phrase "expression control sequence" refers to a nucleic acid that regulates the replication, transcription and translation of a coding sequence in a recipient cell. Examples of expression control sequences include promoter sequences, polyadenylation (pA) signals, introns, transcription termination sequences, enhancers, silencer, upstream regulatory domains, origins of replication, and internal ribosome entry sites ("IRES").

When referring to a nucleic acid molecule or polypeptide, the term "native" refers to a naturally-occurring (e.g., a wild-type (WT)) nucleic acid or polypeptide.

As used herein, the terms "operable linkage" and "operably linked" refer to a physical or functional juxtaposition of the components so described as to permit them to function in their intended manner. In the example of an expression control element in operable linkage with a nucleic acid, the relationship is such that the control element modulates expression of the nucleic acid.

A "vector" is a composition of matter which can be used to deliver a nucleic acid of interest to the interior of a cell, including a nucleic acid molecule capable of transporting another nucleic acid to which it has been linked. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, AAV vectors, retroviral vectors, lentiviral vectors, adenoviral vectors, and the like. An expression construct can be replicated in a living cell, or it can be made synthetically. Vectors capable of directing the expression of genes to which they are operatively linked are often referred to as "expression vectors."

A recombinant "viral vector" is derived from the wild type genome of a virus (e.g., AAV), by using molecular methods to remove the wild type genome from the virus, and replacing it with a non-native nucleic acid, such as a heterologous polynucleotide sequence (e.g., a therapeutic gene or other therapeutic nucleic acid expression cassette). A "recombinant AAV vector" or "rAAV vector" or "rAAV vector genome" is derived from the wild type genome of AAV. Typically, for AAV, one or both inverted terminal repeat (ITR) sequences of the wild type AAV genome are retained in the rAAV vector. A recombinant viral vector (e.g., rAAV, recombinant lentiviral vector) sequence can be packaged into a virus (also referred to herein as a "particle" or "virion") for subsequent infection (transformation) of a cell, ex vivo, in vitro or in vivo. Where a rAAV vector sequence is encapsidated or packaged into an AAV particle, the particle can be referred to as a "rAAV." Such particles or virions include proteins that encapsidate or package the vector genome. Particular examples include viral envelope proteins, and in the case of AAV, capsid proteins (VP1, VP2, VP3). As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Recombinant vectors (e.g., rAAV vectors or plasmids, recombinant lentiviral vectors or plasmids), recombinant viruses or virions (recombinant viral particles), as well as methods and uses thereof, include any viral strain or serotype. A rAAV vector can be based upon an AAV serotype genome distinct from one or more of the capsid proteins that package the vector. rAAV (particles) including rAAV vectors (e.g., recombinant viral genomes) can include at least one capsid protein from a different serotype, a mixture of serotypes, or hybrids or chimeras of different serotypes, such as a VP1, VP2 or VP3 capsid protein of AAV1, AAV2, AAV3, AAV4, AAV5, AAV6, AAV7, AAV8, AAV9, AAV10, AAV11, AAV12, AAV13, AAVrh10, AAV-PHP.5, AAV-PHP.B, AAV-PHP.eB, AAV-retro, or AAV9-retro.

"Purified," as used herein, means separated from many other compounds or entities. A compound or entity (e.g., nucleic acid, protein, virus, viral vector) may be partially purified, substantially purified, or pure. A compound or entity is considered pure when it is removed from substantially all other compounds or entities, i.e., is preferably at least about 90%, more preferably at least about 91%, 92%, 93%, 94%, 95%, 96%.

The phrases "isolated" or "biologically pure" refer to material which is substantially or essentially free from components which normally accompany it as found in its native state.

By "complexed with" "or conjugated to" is meant when one molecule or agent is physically or chemically coupled, adhered, or attached to another molecule or agent either directly or indirectly. For example, in a typical embodiment of a nanoparticle complexed with a nucleic acid encoding pre-miR-7 and polyethylene glycol (PEG), the nanoparticle is coated with (functionalized with) PEG, and the nucleic acid attaches to the PEG, forming a complex. Typically, the nucleic acid attaches or adheres to the PEG via electrostatic interactions.

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and noncovalent (hydrogen bonding, hydrophobic, ionic, and van der waals).

The term "labeled," with regard to a nucleic acid, nanoparticle, virus, peptide, polypeptide, cell, probe or antibody, is intended to encompass direct labeling of the nucleic acid, nanoparticle, virus, peptide, polypeptide, cell, probe or antibody by coupling (i.e., physically linking) a detectable substance to the nucleic acid, nanoparticle, virus, peptide, polypeptide, cell, probe or antibody.

The terms "patient," "subject" and "individual" are used interchangeably herein, and mean a mammalian (e.g., human) subject to be treated, diagnosed, and/or to obtain a biological sample from. Typically, the subject is affected with SCI.

As used herein, the term "therapeutic agent" is meant to encompass any molecule, chemical entity, composition, recombinant virus, nanoparticle, nucleic acid, drug, or biological agent capable of curing, healing, alleviating, relieving, altering, remedying, ameliorating, improving or affecting a disease, the symptoms of disease, or the predisposition toward disease. The term "therapeutic agent" includes natural or synthetic compounds, molecules, chemical entities, compositions, recombinant viruses, nanoparticles, nucleic acids, etc.

As used herein, the terms "treatment" and "therapy" are defined as the application or administration of a therapeutic agent to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease. Methods and uses of the compositions, nanoparticles, vectors, and viruses described herein include treatment methods, which result in any therapeutic or beneficial effect. In particular aspects of the methods and uses of the compositions, nanoparticles, vectors, and viruses disclosed herein, expression of a nucleic acid encoding pre-miR-7 provides a therapeutic benefit to the mammal (e.g., human suffering from SCI). In various embodiments, further included are inhibiting, decreasing or reducing one or more adverse (e.g., physical) symptoms, disorders, illnesses, diseases or complications caused by or associated with a disease (e.g., impaired locomotor function).

By the phrases "therapeutically effective amount" and "effective dosage" is meant an amount sufficient to produce a therapeutically (e.g., clinically) desirable result; for example, the result can be increasing (promoting) neuronal survival and axon regeneration in a subject, improving locomotor function and/or bladder function and/bowel function, and/or alleviating numbness or tingling, in a subject, and treating SCI in a subject (e.g., mammals including humans).

As used herein, "sequence identity" means the percentage of identical subunits at corresponding positions in two sequences when the two sequences are aligned to maximize subunit matching, i.e., taking into account gaps and insertions. Sequence identity is present when a subunit position in both of the two sequences is occupied by the same nucleotide or amino acid, e.g., if a given position is occupied by an adenine in each of two RNA molecules, then the molecules are identical at that position. For example, if 7 positions in a sequence 10 nucleotides in length are identical to the corresponding positions in a second 10-nucleotide sequence, then the two sequences have 70% sequence identity. Sequence identity can be measured using any appropriate sequence analysis software. Because the sequence of miR-7 is conserved between mouse and humans, the sequence of SEQ ID NO: 1 can be used in the compositions, nanoparticles, vectors and viruses described herein for evaluation in mice and humans.

Although compositions, nanoparticles, vectors, viruses, kits, and methods similar or equivalent to those described herein can be used in the practice or testing of the present invention, suitable compositions, nanoparticles, vectors, viruses, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

(FIG. 2A) Sham control without spinal cord injury. (FIG. 2B) Injured spinal cord tissue. Compression injury was performed using a pair of modified forceps with a 0.35 mm spacer attached between the forceps to laterally compress the spinal cord for 15 seconds. Arrowhead indicates injury center and asterisks show cysts at injury area. Bar size is 500 μm.

(FIG. 3A) One μl of AAV1-miR-7 ($6\times10^{13}$ GC/ml) or control AAV1-miR-SC ($6\times10^{13}$ GC/ml) containing scrambled sequence was injected at 3 sites as illustrated. (FIG. 3B) After perfusion using 4% paraformaldehyde, sagittal sectioning was performed on the spinal cord tissue. Because AAV1-miR-7 vector contains eGFP, its successful transduction can be easily monitored using green fluorescence. Images of GFP expression were generated and analyzed at cervical C3-C5, thoracic T7-T9 and lumbar L3-L5 levels of the spinal cord for AAV-miR-7 injections, as well as thoracic T7-T9 for sham control. Bar indicates 50 μm. (FIG. 3C) Total RNAs were extracted from 3 mm of T7-T9 spinal cord tissues isolated from mice transduced with AAV1-miR-7 or AAV1-miR-SC, and miR-7 expression levels were measured using real time PCR (Exiqon). Asterisk indicates a significant difference *$p<0.05$ assessed by t-test. Data are shown as means±SEM. n=3 mice for each group.

(FIG. 10E) Mean of NeuN immunoreactivities in the area at 1 mm equidistant rostral, injury center and caudal were analyzed between AAV-mir7 and AAV-mirSC injected tissue section. Asterisks indicate significant differences between the groups: $p<0.01$, *$p<0.001$ as assessed by two-side t-test. Data represent means/standard error of the mean (n=4 mice; in total, 10 slices were analyzed).

DETAILED DESCRIPTION

Figure 1:
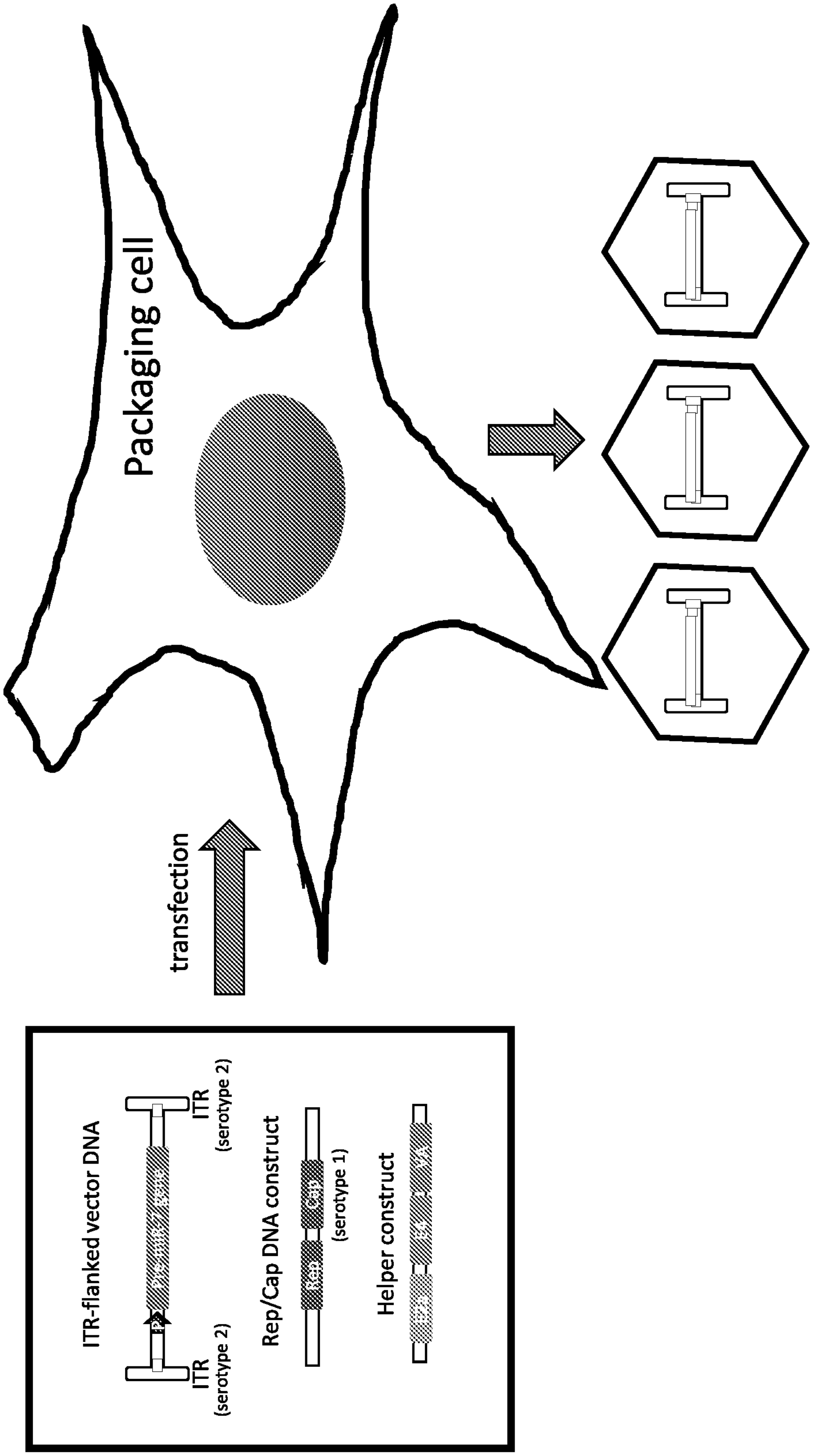
FIG. 1 is an illustration of design and generation of an rAAV1/2, the rAAV tested in the experiments described herein.

Described herein are compositions, nanoparticles, vectors, viruses, and kits including a therapeutically effective amount of pre-miR-7 for improving locomotor function and treating SCI in a subject (e.g., human). Methods of using these compositions, nanoparticles, vectors, viruses, and kits including these compositions, vectors, and viruses are also described herein. It was discovered that pre-miR-7 promotes motor functional recovery following SCI when pre-miR-7 was delivered as AAV1-pre-miR-7 into mouse spinal cord. Using a BMS assay for evaluating locomotor function after SCI, AAV1-pre-miR-7-injected mice had improved locomotor recovery beginning at 1-week post injury and extending until 8-weeks, compared to control (AAV1-miR-SC) mice. Further, several cellular responses were found to be accompanied by the pre-miR-7-mediated motor functional recovery such as attenuation of neuroinflammatory responses, increase of neuronal survival and axon regeneration, and protection of oligodendrocytes. These experimental results demonstrate the efficacy of delivering pre-miR-7 for the treatment of SCI. Embodiments including use of recombinant lentiviral vectors are also described herein.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; The Condensed Protocols From Molecular Cloning: A Laboratory Manual, by Joseph Sambrook et al., Cold Spring Harbor Laboratory Press, Cold Spring Harbor, N.Y., 2006; and Current Protocols in Molecular Biology, ed. Ausubel et al., Greene Publishing and Wiley-Interscience, New York, 1995 (with periodic updates). Conventional methods of gene transfer and gene therapy may also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; Viral Vectors for Gene Therapy: Methods and Protocols, ed. Otto-Wilhelm Merten and Mohammed Al-Rubeai, Humana Press, 2011; and Nonviral Vectors for Gene Therapy: Methods and Protocols, ed. Mark A. Findeis, Humana Press, 2010. Methods for constructing and using viral vectors are known in the art (see, e.g., Miller and Rosman, BioTechniques 1992, 7:980-990). Methods for large-scale production of rAAV are described in Urabe M. J. (2006) Virol. 80:1874-1885; Kotin R. M. (2011) Hum. Mol. Genet. 20:R2-6; Kohlbrenner E. et al. (2005) Mol. Ther. 12:1217-1225; and Mietzsch M. (2014) Hum. Gene Ther. 25:212-222. For a review of rAAV gene therapy methods, see J. L. Santiago-Ortiz and D. V. Schaffer J Control Release 240:287-301, 2016; Rodrigues et al., Pharm Res 36:29, 2019; Choi et al., Curr Gene Ther 5:299-310, 2005; Samulski, R. J. and Muzyczka, N. (2014) AAV-Mediated Gene Therapy for Research and Therapeutic Purposes, Annu. Rev. Virol. 1:427-451. rAAV vectors, variants, chimeras, and rAAV vector mediated gene transfer methods are described in U.S. Pat. No. 9,840,719. Construction, large-scale manufacturing, and clinical use of third-generation SIN lentiviral vectors are well known in the art.

Compositions, Nanoparticles, Gene Therapy Vectors and Viruses for Improving Locomotor Function In a Subject Having a SCI Compositions described herein for improving locomotor function in a subject having a SCI include a therapeutically effective amount of a nucleic acid sequence encoding pre-miR-7. In some embodiments, the nucleic acid sequence encoding pre-miR-7 is complexed with a nanoparticle (e.g., a gold nanoparticle) and PEG. In other embodiments, the nucleic acid sequence encoding pre-miR-7 is included within a gene therapy vector (a gene therapy vector including a polynucleotide sequence including a nucleic acid sequence encoding pre-miR-7). The compositions can also include a pharmaceutically acceptable carrier.

In embodiments in which the nucleic acid sequence encoding pre-miR-7 is included within a gene therapy vector, it is typically contained with a viral vector. The vectors may be episomal, or may be integrated into the target cell genome, through homologous recombination or random integration. Any suitable viral vector can be used. Viruses are naturally evolved vehicles which efficiently deliver their genes into host cells and therefore are desirable vector systems for the delivery of therapeutic nucleic acids. Preferred viral vectors exhibit low toxicity to the host cell and produce/deliver therapeutic quantities of the nucleic acid of interest (in some embodiments, in a tissue-specific manner). A number of viral based systems have been developed for gene transfer into mammalian cells. For example, AAV provide a convenient platform for gene delivery systems. As another example, retroviruses provide a convenient platform for gene delivery systems. In yet other examples, adenovirus vectors, retrovirus vectors, herpesvirus vectors, alphavirus vectors, or lentivirus vectors are used. A selected nucleic acid sequence can be inserted into a vector (a vector genome) and packaged in viral particles using techniques known in the art (e.g., an rAAV vector packaged in rAAV particles, Vesicular stomatitis virus (VSV) G-pseudotyped lentivirus, etc.). The recombinant virus can then be isolated and delivered to cells of the subject.

In the experiments described herein, locomotor function was improved in an SCI mouse model by delivering a nucleic acid sequence encoding pre-miR-7, and in these experiments, a nucleic acid sequence encoding pre-miR-7 was contained within a rAAV vector (serotype 2) packaged in a rAAV having serotype 1 capsid proteins, referred to as rAAV1/2 and illustrated in FIG. 1. However, any suitable rAAV vector can be used. Recombinant AAV vectors include AAV1, AAV2, AAV3, AAV4, AAV5, AAV6, AAV7, AAV8, AAV9, AAV10, AAV11, Rh10, Rh74 or AAV-2i8, and variants thereof. Examples of rAAV can include capsid sequence of any of AAV1, AAV2, AAV3, AAV4, AAV5, AAV6, AAV7, AAV8, AAV9, AAV10, AAV11, Rh10, Rh74 or AAV-2i8, or a capsid variant of AAV1, AAV2, AAV3, AAV4, AAV5, AAV6, AAV7, AAV8, AAV9, AAV10, AAV11, Rh10, Rh74 or AAV-2i8. Particular capsid variants include capsid variants of AAV1, AAV2, AAV3, AAV4, AAV5, AAV6, AAV7, AAV8, AAV9, AAV10, AAV11, Rh10, Rh74 or AAV-2i8, such as a capsid sequence with an amino acid substitution, deletion or insertion/addition. AAV vectors can include additional elements that function in cis or in trans. In particular embodiments, an rAAV vector that includes a vector genome also has: one or more inverted terminal repeat (ITR) sequences that flank the 5' or 3' terminus of the nucleic acid sequence encoding pre-miR-7; an expression control element that drives transcription (e.g., a promoter or enhancer) of the nucleic acid sequence, such as a constitutive or regulatable control element, or tissue-specific expression control element; and/or a poly-Adenine sequence located 3' of the nucleic acid sequence.

In a typical embodiment, an AAV serotype having spinal cord tissue tropism is used. For example, in humans, AAV1 has shown widespread transduction ability and long-lasting gene expression (for reviews of in vivo tissue tropisms, see Nonnenmacher M. and Weber T. (2012) Gene Ther. 19:649-658; Agbandje-McKenna M. and Kleinschmidt J. (2011) AAV capsid and cell interactions—In Adeno-Associated Virus: Methods and Protocols, ed. R O Snyder, P Moullier, p. 47-92, Humana Press, Clifton, NJ; and Asokan A. et al. (2012) Mol. Ther. 4:699-708). In some embodiments, rAAV with serotype 9 capsid proteins is used because rAAV9 has become a preferred vector for CNS delivery due to its increased ability to cross the blood-brain barrier (Lukashchuk V et al. Molecular therapy-Methods and clinical development 3:15055, 2016).

Methods are well known in the art for generating rAAV vectors and rAAV (virions) having improved features for delivering therapeutic agents. rAAV having new capsid variants that, for example, have higher transduction frequency or increased spinal cord tissue tropism, can be used. For example, capsid libraries can be screened in a process called directed evolution (Bartel M. A. (2012) Gene Ther. 19:694-700) to select capsids enriched for infecting a particular tissue or cell type. As another example, rAAV having capsids decorated with ligand targeted to a specific cell type (e.g., spinal cord tissue-specific) can be used. As another example, pseudotyped (also referred to as transcapsidated) rAAV (nucleic acid or genome derived from a first AAV serotype that is encapsidated or packaged by an AAV capsid containing at least one AAV Cap protein of a second serotype (i.e., one different from the first AAV serotype)) can be used. rAAV having mosaic capsids are packaged with a mixture of capsid proteins from two different serotypes. In addition to capsid modifications, rAAV as described herein may include tissue-specific promoters (e.g., spinal cord-specific promoters) and inducible promoters. For a review of rAAV gene therapy methods, see Samulski, R. J. and Muzyczka, N. (2014) AAV-Mediated Gene Therapy for Research and Therapeutic Purposes, Annu. Rev. Virol. 1:427-451. rAAV, variants, chimeras, and rAAV-mediated gene transfer methods are also described in U.S. Pat. No. 9,840,719.

rAAV can be produced using any suitable methods. Methods for large-scale production of rAAV are known and are described in Urabe M. J. (2006) Virol. 80:1874-1885; Kotin R. M. (2011) Hum. Mol. Genet. 20:R2-6; Kohlbrenner E. et al. (2005) Mol. Ther. 12:1217-1225; Mietzsch M. (2014) Hum. Gene Ther. 25:212-222; and U.S. Pat. Nos. 6,436,392, 7,241,447, and 8,236,557. For the experiments described herein, AAV1-miR-7 was ordered from Vector Biolabs (Malvern, PA). The AAV1-miR-7 was produced in HEK293T cells.

Construction, large-scale manufacturing, and clinical use of third-generation SIN lentiviral vectors are well known in the art. See, for example, Ghani et al. Mol Ther Methods Clin Dev. 2019 Sep 13; 14: 90-99; and Hu et al. Mol Ther Methods Clin Dev. 2015; 2: 15004.

The viral vectors described herein typically include one or more expression control elements. Expression control elements include ubiquitous or promiscuous promoters/enhancers which are capable of driving expression of a polynucleotide (nucleic acid) in many different cell types. Such elements include, but are not limited to the EF1a promoter, the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature, the SV40 promoter, the dihydrofolate reductase (DHFR) promoter, the cytoplasmic β-acctin promoter, the phosphoglycerol kinase (PGK) promoter, etc.

Expression control elements include those active in a particular tissue or cell type, referred to herein as a "tissue-specific expression control elements/promoters." Tissue-specific expression control elements are typically active in a specific cell or tissue (e.g., spinal cord). Expression control elements also can confer expression in a manner that is regulatable, that is, a signal or stimuli increases or decreases expression of the operably linked nucleic acid. A regulatable element that increases expression of the operably linked nucleic acid in response to a signal or stimuli is also referred to as an "inducible element" (i.e., is induced by a signal). A regulatable element that decreases expression of the operably linked nucleic acid in response to a signal or stimuli is referred to as a "repressible element" (i.e., the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression.

Expression control elements also include native elements(s). A native control element (e.g., promoter) may be used when it is desired that expression of the nucleic acid may mimic the native expression. A native element may be used when expression of the nucleic acid is to be regulated temporally or developmentally, or in a tissue-specific manner, or in response to specific transcriptional stimuli. Other native expression control elements, such as introns, polyadenylation sites or Kozak consensus sequences may also be used.

As indicated above, in some embodiments, a composition for improving locomotor function in a subject having a SCI includes a nanoparticle complexed with PEG and a nucleic acid sequence encoding pre-miR-7. In general, nanoparticles contemplated include any compound or substance with a high loading capacity for a nucleic acid (e.g., pre-miR-7) as described herein, including for example and without limitation, a metal, a semiconductor, and an insulator particle composition, and a dendrimer (organic versus inorganic). Thus, nanoparticles are contemplated which include a variety of inorganic materials including, but not limited to, metals, semi-conductor materials or ceramics. In one embodiment, the nanoparticle is metallic, and in various aspects, the nanoparticle is a colloidal metal. Thus, in various embodiments, nanoparticles of the invention include metal (including for example and without limitation, gold, silver, platinum, aluminum, palladium, copper, cobalt, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials. Nanoparticles as described herein include those that are available commercially (e.g., Nanohybrids), as well as those that are synthesized, e.g., produced from progressive nucleation in solution (e.g., by colloid reaction) or by various physical and chemical vapor deposition processes. Methods of making metal, semiconductor and magnetic nanoparticles are well-known in the art. Nanoparticles such as gold nanoparticles can be produced using any suitable methods, e.g., those described in Papastefanaki et al. Mol Ther 23:993-1002, 2015; Kao et al. Nanotechnology 25:295102, 2015; Gerard et al. Pain 156:1320-1333, 2015; Bonoiu et al. Proc Natl Acad Scie USA 106:5546-5550; Schmid, G. (ed.) Clusters and Colloids (VCH, Weinheim, 1994); Hayat, M. A. (ed.) Colloidal Gold: Principles, Methods, and Applications (Academic Press, San Diego, 1991); Burda et al., Chem. Rev. 105: 1025-1102, 2005; Daniel and Astruc Chem. Rev. 104: 293-346, 2004' and U.S. Pat. nos. 10,391,116, 10,370,661 and 9382346.

Nanoparticles can range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm, from about 10 to 150 nm, from about 10 to about 100 nm, or about 10 to about 50 nm. Typically, the size of the nanoparticles is from about 5 nm to about 150 nm (mean diameter), from about 30 to about 100 nm, from about 40 to about 80 nm. In some embodiments, the nanoparticle is optionally labeled. In some embodiments, the nanoparticle further includes a targeting molecule.

Methods for Improving Locomotor Function in a Subject Having a SCI

Described herein are methods for promoting functional recovery, including improving locomotor function, in a subject following SCI. In some embodiments, these methods include administering to the subject having a SCI an effective amount of a recombinant virus that includes a recombinant viral vector that contains a polynucleotide sequence including a nucleic acid sequence encoding pre-miR-7, or an effective amount of a composition including the recombinant virus. In other embodiments, these methods include administering to the subject a nanoparticle complexed with PEG and a nucleic acid sequence encoding pre-miR-7 (e.g., administering a gold nanoparticle to a human). Typically, the compositions, nanoparticles, gene therapy vectors and recombinant viruses are delivered to appropriate target cells in the subject (e.g., human patient). A typical target cell is any neuron, glial cell, or oligodendrocyte.

In some embodiments of a method for promoting functional recovery in a subject following SCI, a rAAV including a rAAV vector including a polynucleotide sequence including a nucleic acid sequence encoding pre-miR-7 is adminsitered to the subject in a therapeutically effective amount for improving locomotor function. In such embodiments, the rAAV can include serotype 1 or 9 capsid proteins and the rAAV vector can be serotype 2. In other embodiments of a method for promoting functional recovery in a subject following SCI, a lentivirus system including a recombinant lentiviral vector that includes a polynucleotide sequence including a nucleic acid sequence encoding pre-miR-7 is adminsitered to the subject in a therapeutically effective amount for improving locomotor function.

Typically, the recombinant virus is administered to the subject at one of the following time points: within 1 hour of SCI injury, within 2 hours of SCI injury, within 4 hours of SCI injury, within 6 hours of SCI injury, within 8 hours of SCI injury, within 12 hours of SCI injury, within 24 hours of SCI injury, within 48 hours of SCI injury, within 72 hours of SCI injury, within 7 days of SCI injury, and within one month of SCI injury. In some embodiments, a single adminsistration is sufficient for promoting functional recovery in a subject following SCI, as the spinal cord cells are transduced with a viral vector, and the vector expresses itself on an ongoing (e.g., long-term) basis. In some embodiments in which the composition, nanoparticle, gene therapy vector or recombinant virus is directly injected into the subject's spinal cord, two or more (multiple) administrations at two or more time points (e.g., over weeks, over months) are performed.

The methods include administration of any of the compositions, nanoparticles, gene therapy vectors and recombinant viruses described herein. Administration of a composition, nanoparticle, vector or virus as described herein to a subject having a SCI results in one or more of: increased neuronal survival, increased axon regeneration, improved bladder function, improved locomotor function, improved bowel function, and alleviating numbness and/or tingling, in the subject. The methods can further include evaluating one or more of locomotor function, bladder function, bowel function, numbness, and tingling in the subject at a time point subsequent to administration of the composition, nanoparticle, gene therapy vector, or recombinant virus.

Combination therapies may be used to improve locomotor function and treat SCI in a subject. In some embodiments, a combination therapy involves administering a composition including a nucleic acid sequence encoding pre-miR-7 (e.g., nanoparticle composition or gene therapy vector as described herein) and a second SCI therapeutic. In such an embodiment, the composition and the second SCI therapeutic can be administered in the same composition simultaneously, or they can be administered at different time points (e.g., two different compositions administered at two different time points). In any combination therapy, the two or more therapeutics can be administered simultaneously, concurrently or sequentially, e.g., at two or more different time points. Typically, such a combination therapy increases neuronal survival and axon regeneration and improves bladder function, bowel function and locomotor function, and alleviates numbness and/or tingling in the subject. In one embodiment of combination therapy, a composition including a nucleic acid sequence encoding pre-miR-7 and a second SCI therapeutic are admixed in the same injection or infusion volume.

Any suitable methods of administering such a composition, nanoparticle, virus or vector to a subject may be used. In these methods, the compositions, nanoparticles, viruses and vectors can be administered to a subject by any suitable route, e.g., injection directly into the target site (e.g., spinal cord), intravenous (IV) administration, etc. The compositions may be administered by catheter to a site accessible by a blood vessel. If administered via intravenous injection, the compositions, nanoparticles, vectors and viruses may be administered in a single bolus, multiple injections, or by continuous infusion (e.g., intravenously, pump infusion). For parenteral administration, the compositions are preferably formulated in a sterilized pyrogen-free form.

The compositions described herein may be in a form suitable for sterile injection. To prepare such a composition, the suitable active therapeutic(s) (e.g., a nucleic acid encoding pre-miR-7, a vector encoding same, a recombinant virus, a nanoparticle complexed with a nucleic acid encoding pre-miR-7) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the therapeutics is only sparingly or slightly soluble in water, a dissolution enhancing or solubilizing agent can be added, or the solvent may include 10-60% w/w of propylene glycol or the like. The compositions, viruses and viral vectors described herein may be administered to mammals (e.g., rodents, humans, nonhuman primates, canines, felines, ovines, bovines) in any suitable formulation according to conventional pharmaceutical practice (see, e.g., Remington: The Science and Practice of Pharmacy (20th ed.), ed. A. R. Gennaro, Lippincott Williams & Wilkins, (2000) and Encyclopedia of Pharmaceutical Technology, eds. J. Swarbrick and J. C. Boylan, Marcel Dekker, New York (1988-1999), a standard text in this field, and in USP/NF). A description of exemplary pharmaceutically acceptable carriers and diluents, as well as pharmaceutical formulations, can be found in Remington: supra. Other substances may be added to the compositions to stabilize and/or preserve the compositions. As used herein the terms "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a nanoparticle, viral vector or viral particle to a subject.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Viral vectors (e.g., AAV vectors), viruses, nanoparticles, and pharmaceutical compositions thereof, can be packaged in single or multiple unit dosage form for ease of administration and uniformity of dosage.

Effective Doses

The compositions, nanoparticles, viruses and vectors described herein are preferably administered to a mammal (e.g., human) in an effective amount, that is, an amount capable of producing a desirable result in a treated mammal (e.g., increasing neuronal survival and axon regeneration, improving bladder function, bowel function and locomotor function, alleviating numbness and/or tingling). Such a therapeutically effective amount can be determined according to standard methods. Toxicity and therapeutic efficacy of the compositions, nanoparticles, viruses and vectors utilized in methods of the invention can be determined by standard pharmaceutical procedures. As is well known in the medical and veterinary arts, dosage for any one subject depends on many factors, including the subject's size, body surface area, age, the particular composition to be administered, time and route of administration, general health, and other drugs being administered concurrently. A delivery dose of a composition, nanoparticle, virus or vector as described herein is determined based on preclinical efficacy and safety. In some embodiments wherein the nanoparticle or gene therapy vector is injected into the subject's spinal cord, a therapeutically effective amount (e.g., an appropriate dose) for a human would be between about 10 μl and 10 ml (e.g., 10 μl, 100 μl, 1 ml, 10 ml). Typically, the range of titer of the viral vector is about $6\times10^{13}$ to about $1\times10^{15}$.

Kits

Described herein are kits for improving locomotor function in a subject (e.g., a human) having a SCI. A typical kit includes a composition including a pharmaceutically acceptable carrier (e.g., a physiological buffer) and a therapeutically effective amount of a nucleic acid sequence encoding pre-miR-7; and instructions for use. In some embodiments, a kit for combination therapy will also include a second SCI therapeutic (e.g., a kit containing a gene therapy vector including a polynucleotide sequence including a nucleic acid sequence encoding pre-miR-7and a second SCI therapeutic). Kits also typically include a container and packaging. Instructional materials for preparation and use of the compositions, nanoparticles, viruses and vectors described herein are generally included. While the instructional materials typically include written or printed materials, they are not limited to such. Any medium capable of storing such instructions and communicating them to an end user is encompassed by the kits herein. Such media include, but are not limited to electronic storage media, optical media, and the like. Such media may include addresses to internet sites that provide such instructional materials.

EXAMPLES

The present invention is further illustrated by the following specific examples. The examples are provided for illustration only and should not be construed as limiting the scope of the invention in any way.

Example 1 — Recombinant Viral Vector Delivery of pre-miR-7

Figures 2A, 2B:
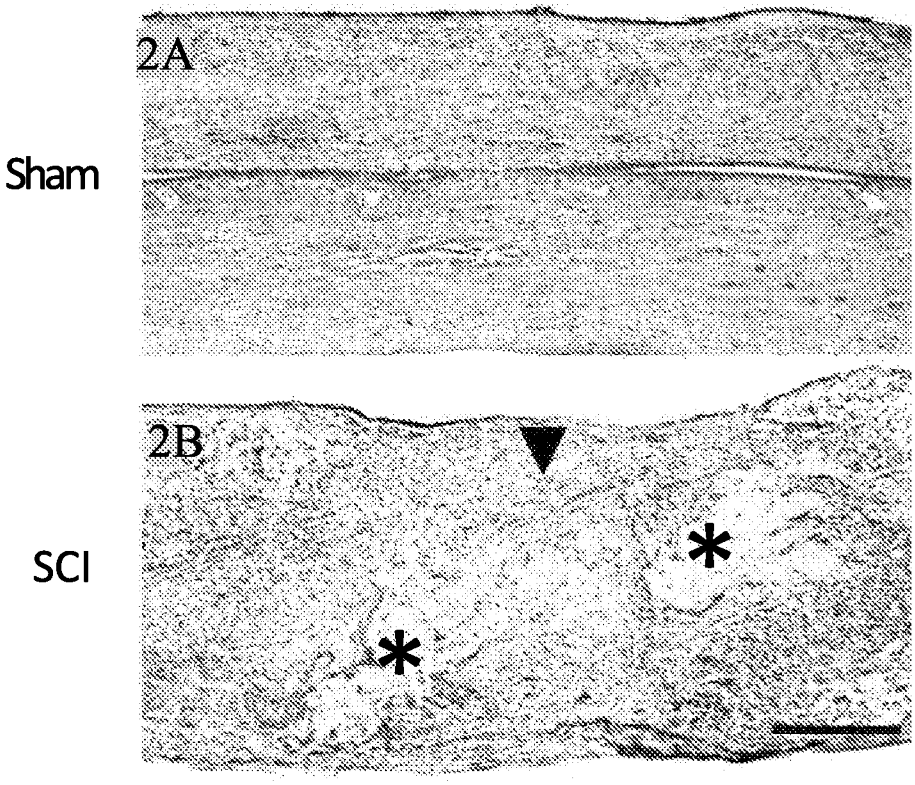
FIGS. 2A and 2B are a pair of images showing Hematoxilin and Eosin (H&E) staining showing injured area including cyst from compressed spinal cord. The mice were perfused and sagittal spinal cord sections were analyzed by H&E staining to detect the injury area at 1 week post compression injury.

Adeno Associated Virus 1 (AAV1)-mediated Delivery of Pre-miR-7:

A compression injury model was employed because compression spares some spinal cord tissue depending on the severity, which is more relevant to clinical conditions. Mice received severe compression injury in the spinal cord exhibited flaccid paralysis of the lower extremities, and showed cellular disorganization/tissue loss near the injury epicenter as compared with sham (non-injured) controls (FIGS. 2A, 2B).

As an initial attempt to deliver lentivirus expressing pre-miR-7 led to only marginal increase of miR-7 expression, a rAAV was chosen to deliver pre-miR-7 into the mouse spinal cord. See FIG. 1 for an illustration of this rAAV in which the ITRs are serotype 2 and the capsid proteins are serotype 1 (generally referred to as "rAAV1/2"). AAV1-miR-7 was obtained from Vector Biolabs Inc (Malvern, PA), which expresses a precursor form of miR-7. The AAV1 serotype was selected due to its widespread transduction ability and long-lasting expression. As a negative control, AAV1-control (AAV1-miR-SC) was obtained, which contains a scrambled sequence.

Figures 3A, 3B, 3C:
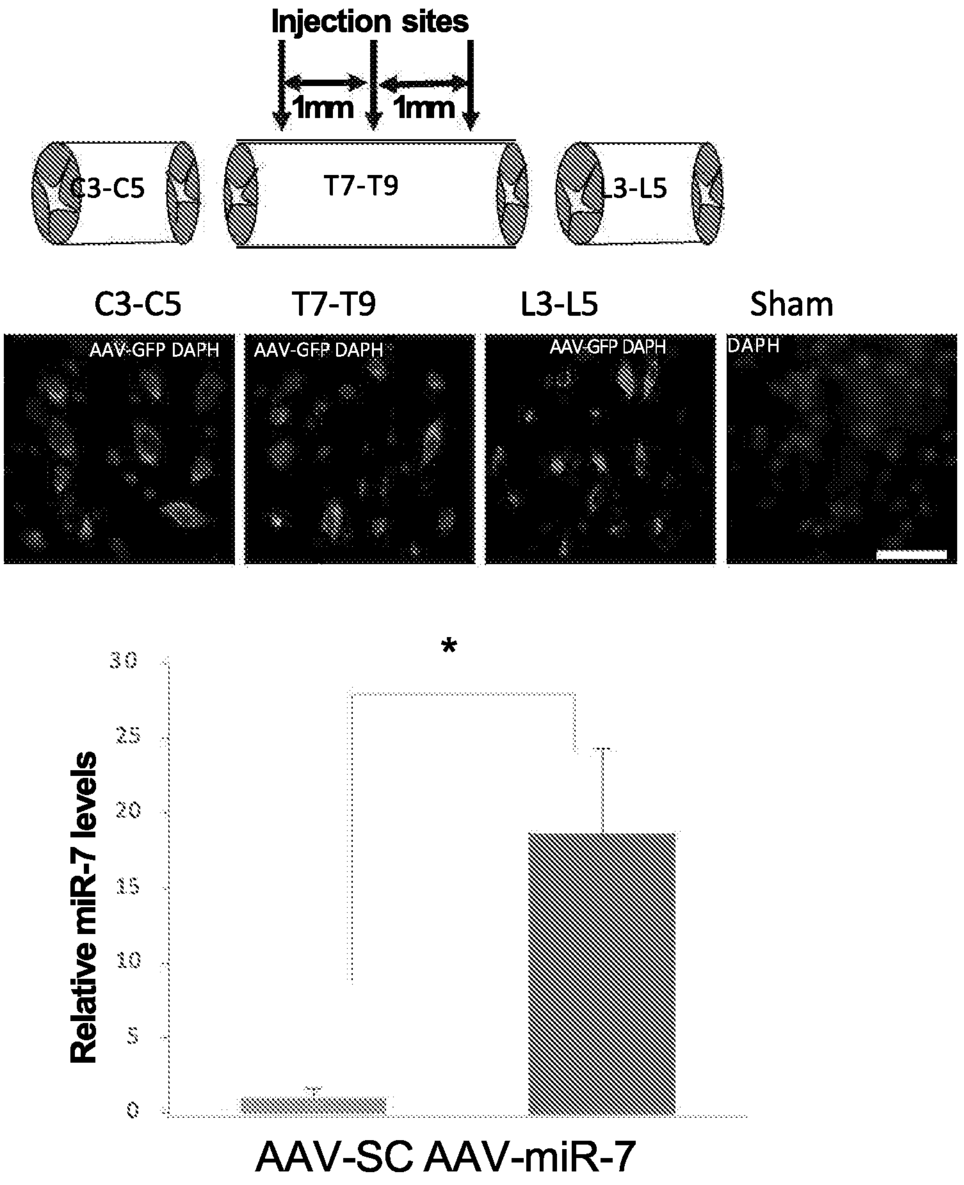
FIGS. 3A, 3B and 3C are an illustration of injection sites, fluorescence images, and a graph showing successful transduction of AAV1-miR-7 in spinal cord at 4 weeks.
Figures 4A, 4B, 4C, 4D:
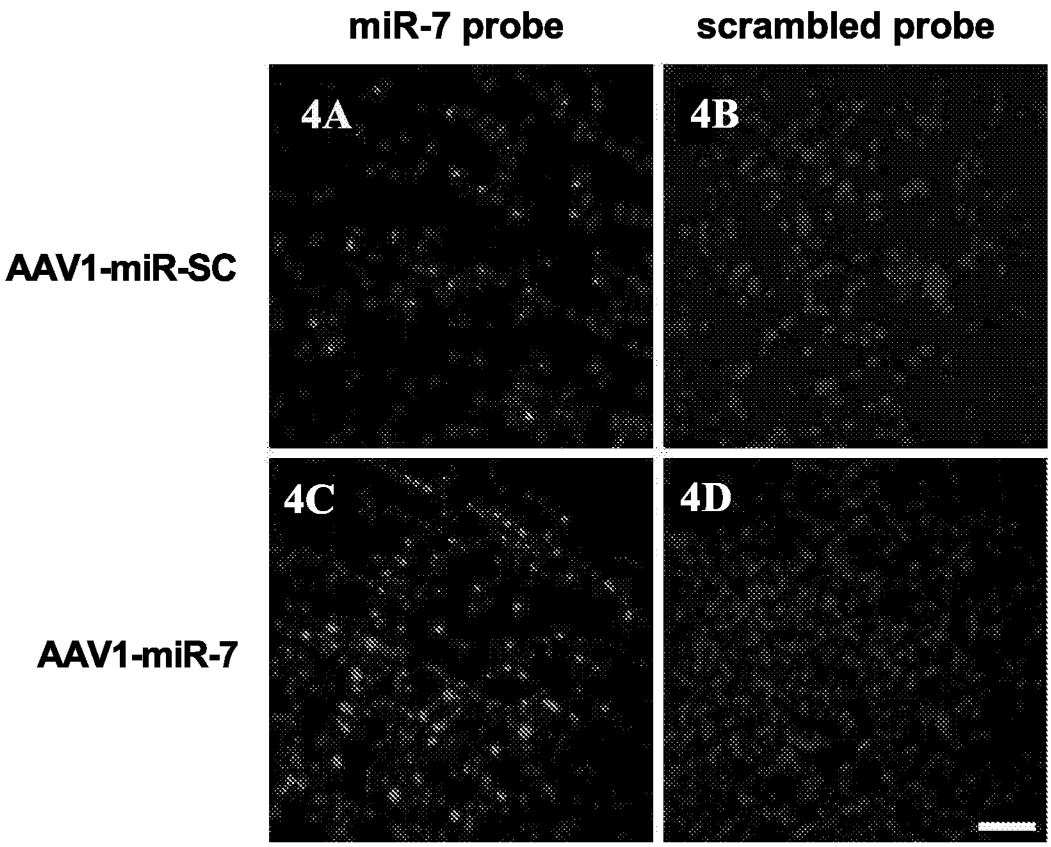
FIGS. 4A, 4B, 4C and 4D are a series of fluorescence images showing in situ hybridization detecting miR-7 expression in the mouse spinal cord. One μl of AAV-miR-7 or AAV-miR-SC was injected at injury center, 1 mm rostral, and 1 mm caudal from injury center. After 4 weeks post injury, in situ hybridization with a probe to detect miR-7 expression was performed (FIGS. 4A, 4C). As a negative control, a control scrambled sequence probe was used not to bind to any miRs (FIGS. 4B, 4D). AAV1-miR-7 transduced sample shows the highly increased miR-7 expression (red signal). Note the endogenous level of miR-7 in the AAV1-miR-SC sample as well. The bar indicates 50 μm.

Transduction and Expression of AAV1-miR-7 in the Mouse Spinal Cord:

First, the successful transduction of AAV1-miR-7 and expression of miR-7 in the spinal cord was confirmed. Because AAV1-miR-7 vector contains eGFP, its successful transduction can be easily monitored using green fluorescence. One microliter of AAV1-miR-7 or AAV1-miR-SC was injected to the injury center, 1 mm rostral, and 1 mm caudal from the center of injured spinal cord at a depth of 1 mm (FIG. 3A). As shown in FIG. 3B, AAV1 injection led to successful transduction in spinal cord tissues at 4-weeks post infection. Further, green fluorescence-containing cells were also observed in cervical and lumbar regions of spinal cord, indicating that transduction of AAV1 occurred places distant to injection sites. Next, the expression level of the mature form of miR-7 from thoracic region of spinal cord tissue was determined. As shown in FIG. 3C, transduction of AAV1-miR-7 led to a huge increase (about 20-fold) of miR-7 expression, compared to AAV1-miR-SC injected samples. In addition, successful overexpression of miR-7 due to AAV1-miR-7 transduction in injured mice was also confirmed by in situ hybridization of miR-7 (FIGS. 4A-4D). Compared to lentiviral—mediated miR-7 delivery experiments, the overexpression of miR-7 using AAV1-mediated delivery of miR-7 in the mouse spinal cord achieved a more successful result.

Figure 5:
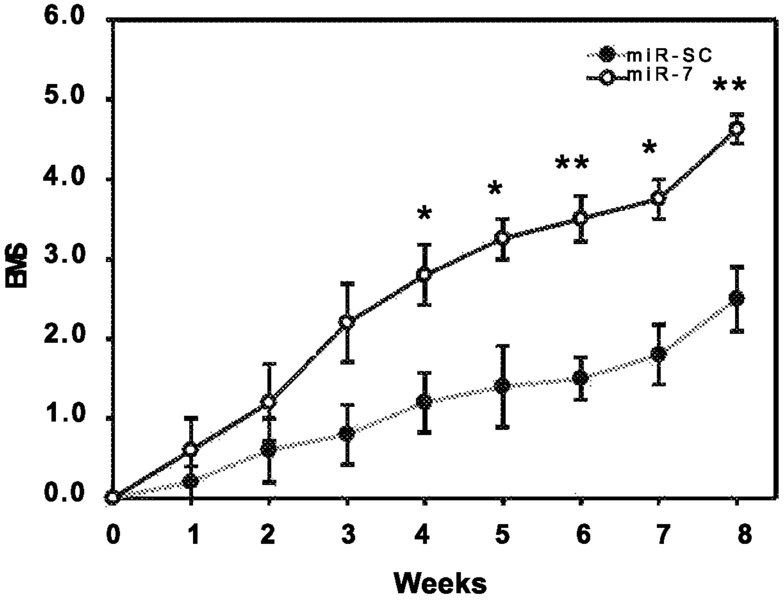
FIG. 5 is a graph showing locomotor recovery of AAV1-miR-7 injected mice following severe compression spinal cord. The Basso Mouse Scale (BMS) was used to score locomotor recovery up to 8-weeks post injury. Asterisks indicate significant differences *$p<0.05$, **$p<0.01$ assessed by t-test. Data are shown as means±SEM. n=6 mice for each group.
Figures 6A, 6B, 6C, 6D, 6E, 6F, 6G:
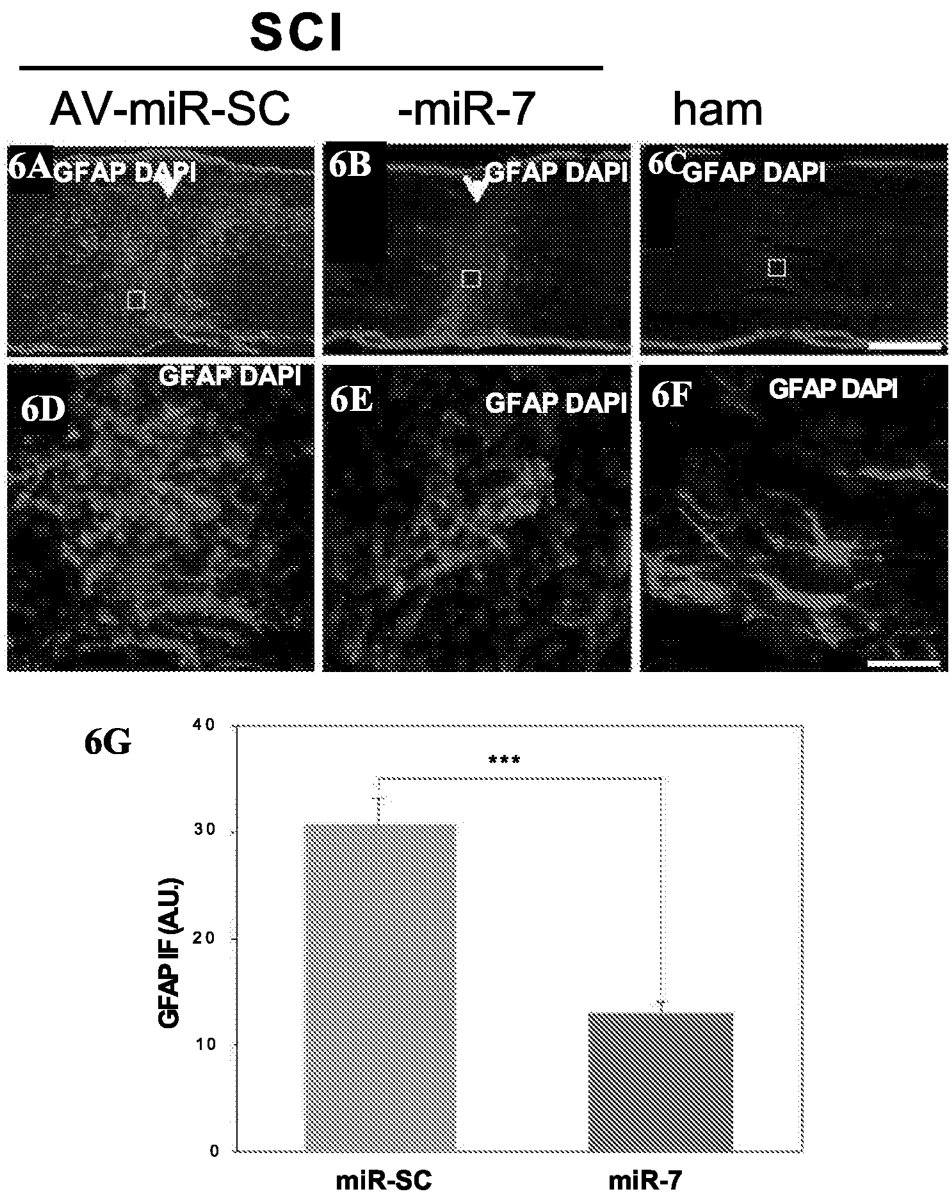
FIGS. 6A, 6B, 6C, 6D, 6E, 6F and are a series of fluorescence images and a graph showing reduced astrocyte activation by AAV1-miR-7 transduction at 4 weeks post-injury. Representative images of sagittal sections showing Glial fibrillary acidic protein (GFAP)-reactive astrocytes are shown (FIGS. 6A-6C). Sections were stained with anti-GFAP antibody (1:300, cat #GA52461-2, Agilent-Dako, Santa Clara, CA). Higher magnification images from the boxed area are shown for each figure (FIGS. 6D-6F). Staining intensities of the entire images (FIGS. 6A and 6B) were quantified using ImageJ software (FIG. 6G). Arrows indicate the injury center and bars indicate 400 μm (FIGS. 6A-6C) and 50 μm (FIGS. 6D-6F), respectively. ***$p<0.001$ assessed by t-test. Data represent means±SEM, (n=4 mice).
Figures 7A, 7B, 7C, 7D:
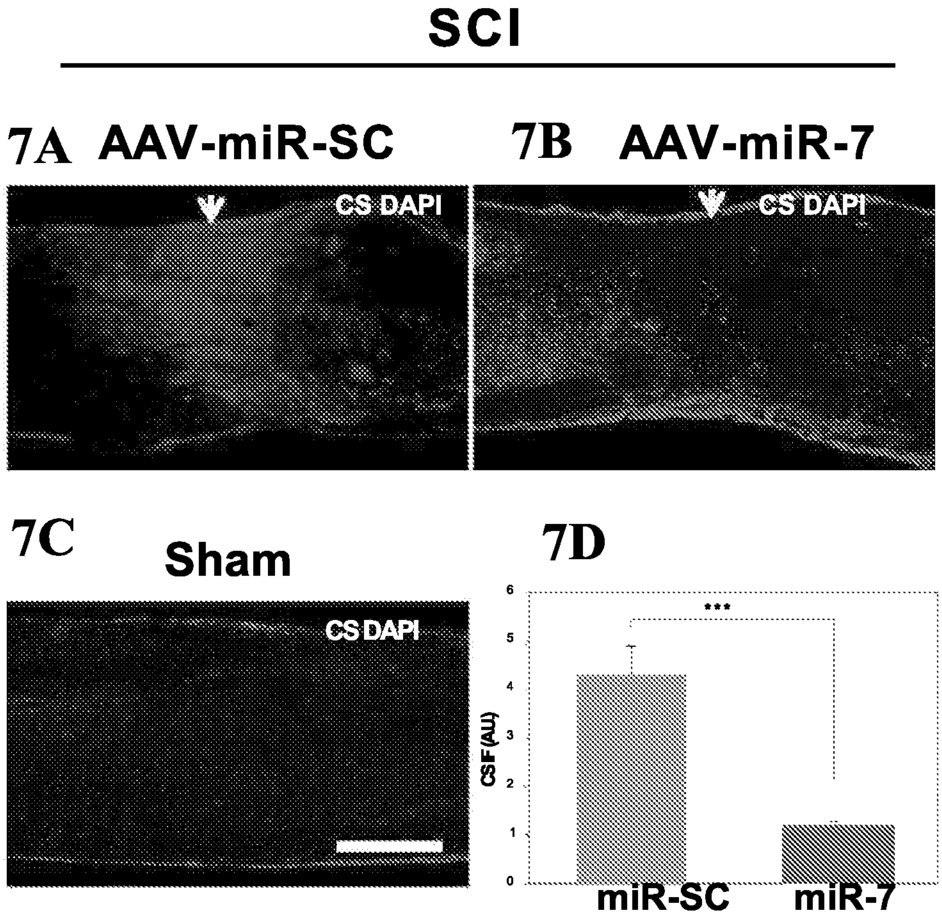
FIGS. 7A, 7B, 7C and 7D are a series of fluorescence images and a graph showing reduced production of Chondroitin Sulfate (CS) by AAV1-miR-7 transduction at 4 weeks post-injury. Representative images of sagittal sections stained with anti-chondroitin sulfate antibody (CS-56) (1:200, cat #C8035, Sigma-Aldrich, St. Louis, MO) are shown (FIGS. 7A-7C) including a sham control. Staining intensities of the entire images (FIGS. 7A and 7B) were quantified using ImageJ software (FIG. 7D). Arrowheads indicate the injury center and bars indicate 400 μm. ***$p<0.001$ assessed by t-test. Data represent means±SEM, (n=4 mice).
Figures 8A, 8B, 8C, 8D, 8E, 8F, 8G:
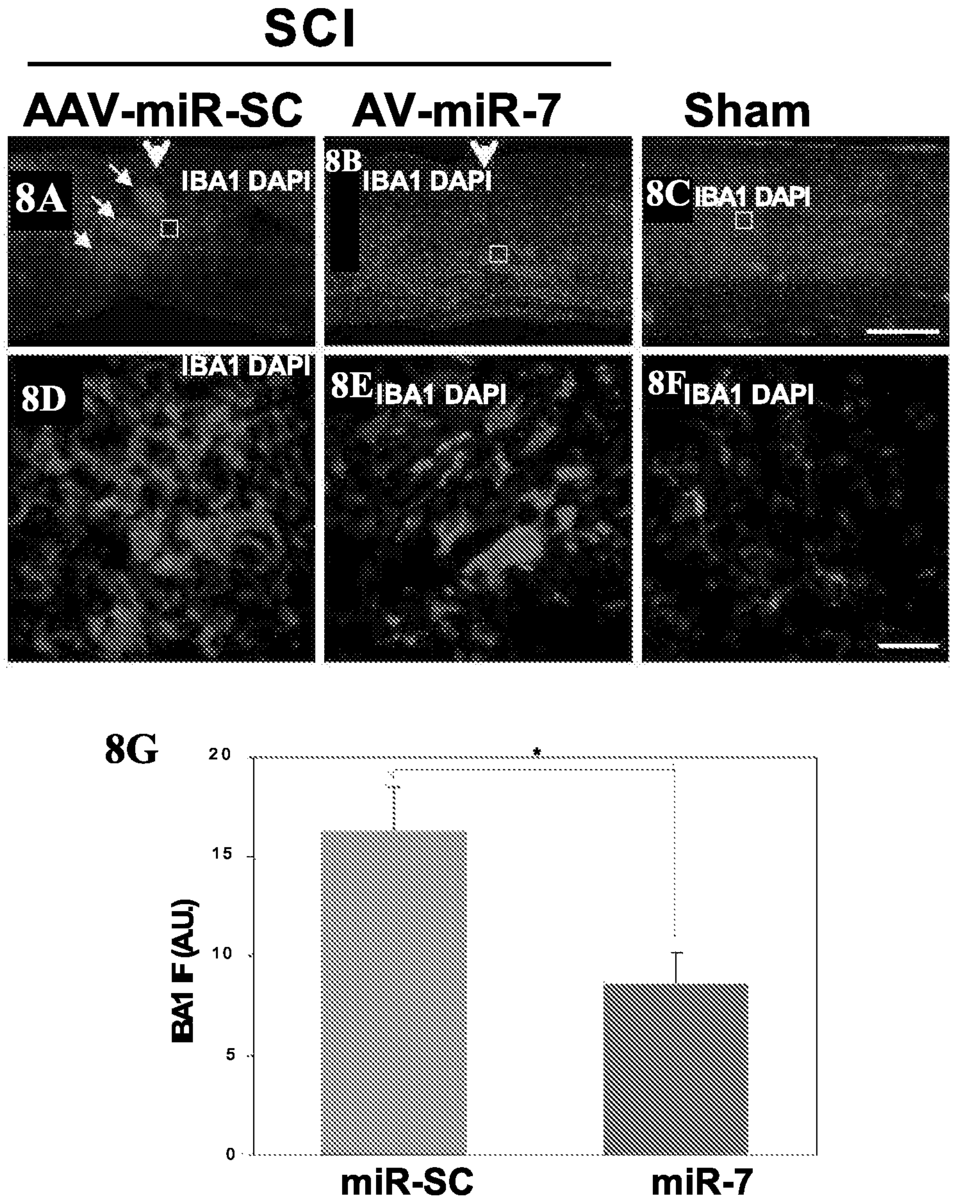
FIGS. 8A, 8B, 8C, 8D, 8E, 8F and 8G are a series of fluorescence images and a graph showing reduced microglial/macrophage activation by AAV1-miR-7 transduction at 4 weeks post-injury. Representative images of sagittal sections showing Iba1-reactive microglia/macrophage are shown (FIGS. 8A-8C). Sections were stained with anti-Iba1 antibody (1:800, cat #019-19741, Wako, Osaka, Japan). Iba1 is a marker for microglia. Higher magnification images from the boxed area are shown for each figure (FIGS. 8D-8F). Staining intensities of the entire images (FIGS. 8A and 8B) were quantified using ImageJ software (FIG. 8G). Arrows indicate the injury center and bars indicate 400 μm (FIGS. 8A-8C) and 50 μm (FIGS. 8D-8F), respectively. *$p<0.05$ assessed by t-test. Data represent means±SEM, (n=4 mice).
Figures 9A, 9B, 9C, 9D, 9E, 9F, 9G, 9H, 9I, 9J, 9K, 9L:
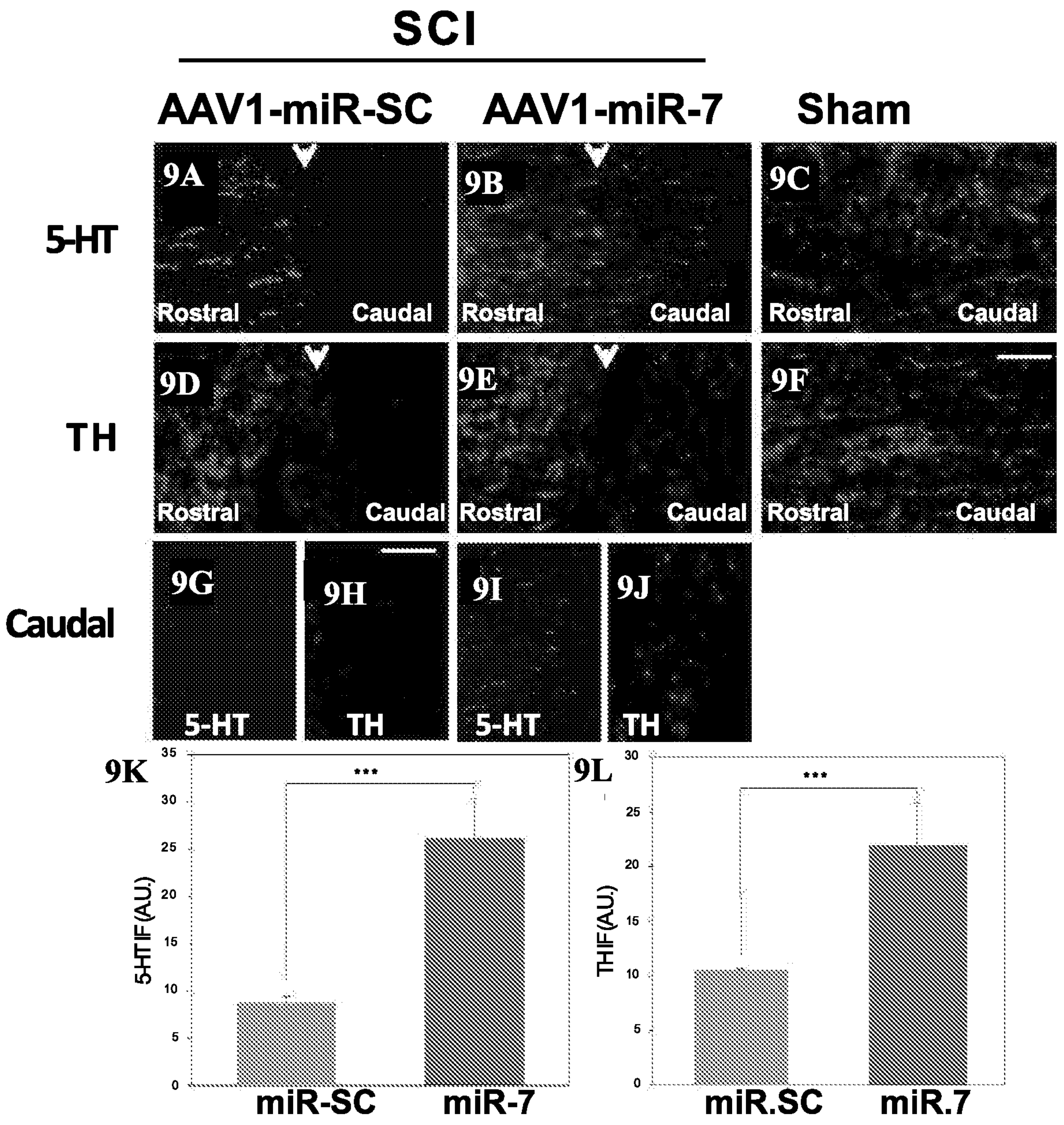
FIGS. 9A, 9B, 9C, 9D, 9E, 9F, 9G, 9H, 9I, 9J, 9K and 9L are a series of fluorescence images and a pair of graphs showing increased 5-hydroxytryptamine (5-HT) or tyrosine hydroxylase (TH)-positive axons in the caudal region to injury center by AAV1-miR-7 transduction at 4 weeks post-injury. Representative images of sagittal sections stained with 5-HT antibody (1:400, cat #10385, Abcam, Cambridge, MA) or TH antibody (1:500, cat #AB152, Millipore, Temecula, CA) are shown (FIGS. 9A-9E). In addition, the images of caudal region are shown (FIGS. 9G-9J), and signal intensities were calculated from these figures (FIGS. 9G-9J) and shown in graphs (FIGS. 9K and 9L). Arrow head indicates injury center. Bars indicate 200 μm. ***$p<0.001$ assessed by t-test. Data represent means±SEM, (n=4 mice).
Figures 10A, 10B, 10C, 10D, 10E:
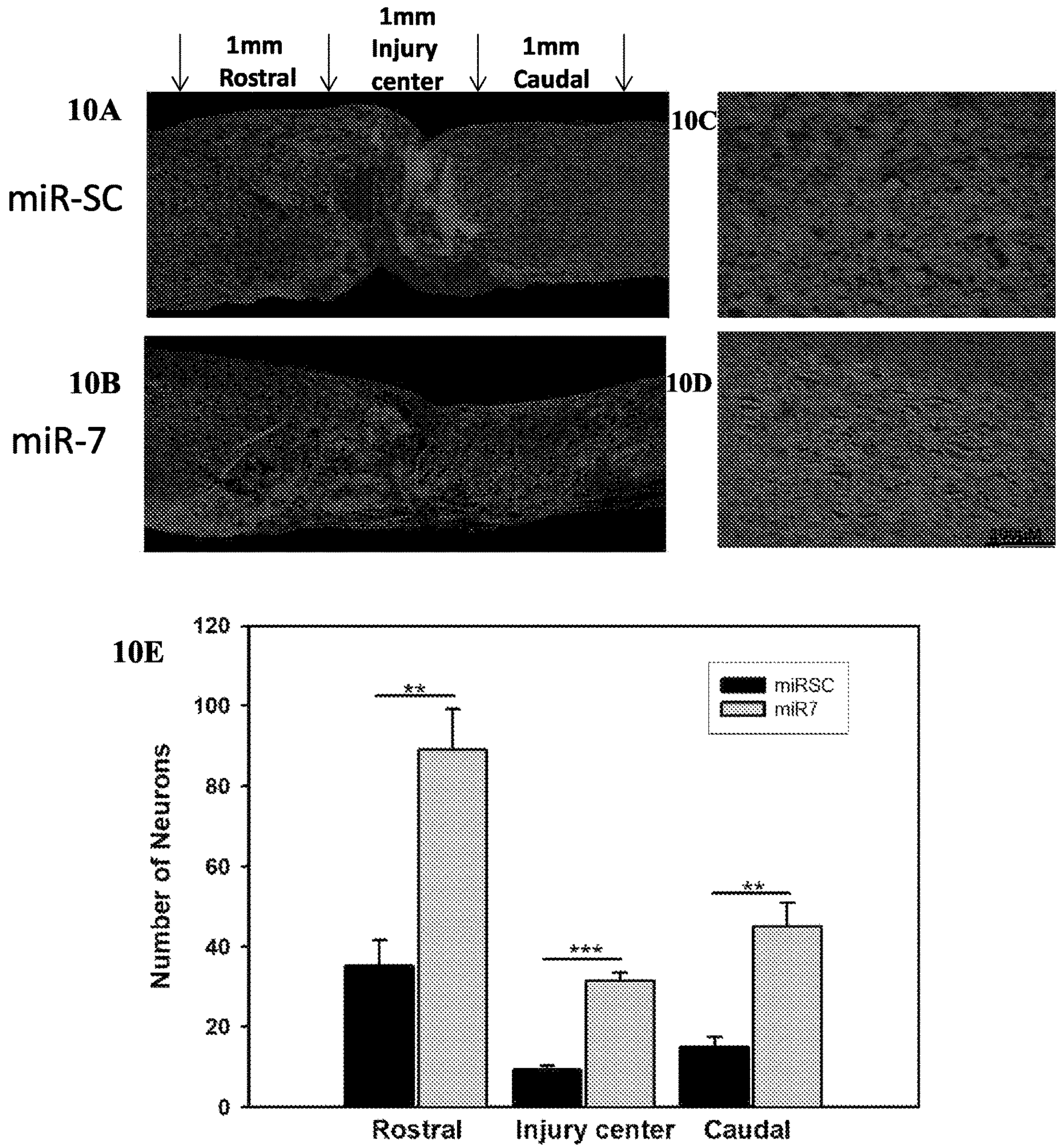
FIGS. 10A, 10B, 10C, 10D and 10E are a series of fluorescence images and a graph showing increased neuronal survival by AAV1-miR-7 transduction at 4 weeks post-injury. Representative images of sagittal sections stained with NeuN antibody are shown. Images containing injury center, rostral and caudal to injury center were taken at lower magnification (FIGS. 10A and 10B) and each image of rostral region has been enlarged and presented (FIGS. 10C and 10D).

Determination of Locomotor Behavior after SCI:

A BMS assay was performed for evaluating locomotor function after SCI. AAV1-miR-7-transduced mice had improved locomotor recovery beginning at 1-week post injury and extending until 8-weeks (FIG. 5), compared to AAV1-miR-SC mice. This result suggests that miR-7 expression may confer neuroprotection and recovery of locomotor function in SCI. Cellular responses accompanying the enhanced motor functional recovery:

Attenuation of neuroinflammatory responses. As astrogliosis following SCI results in a dense scar that hinders axon regeneration, the effect of miR-7 on astrocyte activation was investigated by staining the injured tissues with anti-GFAP antibody. Transduction of AAV1-miR-7 dramatically decreased astrocyte activation at 4 weeks after injury, compared to AAV1-miR-SC (FIGS. 6A-6G). In addition, it is well known that injury to the spinal cord results in increased production of chondroitin sulfate proteoglycans (CSPGs). CSPGs are produced mainly by reactive glia and have been shown to be inhibitory for axon regrowth/regeneration following SCI. Therefore, the effect of miR-7 on CSPGs was evaluated using antibody (CS-56) to detect chondroitin sulfate (CS). As shown in FIGS. 7A-7D, miR-7 expression significantly reduced the CS generation following SCI. Given the multifaceted inhibitory role of CSPGs including neuronal survival, axonal sprouting and remyelination in the injured spinal cord, their manipulation has become a promising therapeutic target for SCI. In addition, it is reported that activation of microglia/macrophages aggravates injury and leads to poor recovery. Iba1-positive microglia/macrophages persisted at the injury site in the AAV1-miR-SC-transduced mice following SCI, whereas Iba1-positive microglia/macrophages were significantly reduced in the AAV1-miR-7 samples (FIGS. 8A-8G), suggesting that miR-7 inhibits the microglia/macrophage activation. Conclusively, miR-7 expression inhibits the neuroinflammatory response, and subsequently promotes motor functional recovery following SCI.

TABLE 1

Potential target genes of miR-7 in CSPG biosynthesis pathway.

| Gene Symbol | Gene Name | Predicted binding region |
|---|---|---|
| CSPG5 | Chondroitin sulfate proteoglycan 5 | ORF |
| CHST3 | carbohydrate sulfotransferase 3 | 3'-UTR |
| CHST9 | Carbohydrate sulfotransferase 7 | ORF |

TABLE 2

Additional potential target genes of miR-7 in CSPG biosynthesis pathway.

| Gene Symbol | Gene Name | miTG score |
|---|---|---|
| B3GAT1 | beta-1,3-glucuronyltransferase 1 | 0.795 |
| CHST12 | carbohydrate sulfotransferase 12 | 0.692 |
| CHST13 | carbohydrate sulfotransferase 13 | 0.688 |

miTG score is obtained from DIANA-microT-CDS algorithm. The higher the miTG score the higher the probability of targeting, ranging from 0.3-1.0. Score>0.7 is considered high prediction.

Increase of axon regeneration. To analyze the level of spared and regenerating axons in the lesion site, the immunoreactivities of serotonergic (5-HT) and tyrosine hydroxylase (TH) positive axons caudal to the injury site was determined. As shown in FIGS. 9A-9L, mice transduced with AAV1-miR-7 have more 5-HT-positive axons and TH-positive axons, compared to AAV1-miR-SC. These observations suggest that axonal regeneration following SCI is enhanced upon transduction of AAV1-miR-7.

Increase of neuronal survival. To determine the effect of miR-7 expression on survival of neurons post injury, the neuronal sparing in the epicenter region of injury was assessed. Sagittal sections stained against NeuN, a neuronal marker, showed a greater number of neurons at injury regions in AAV1-miR-7 mice compared to control mice (FIGS. 10A-10E), suggesting that miR-7 expression attenuated the neuronal loss after injury.

Figures 11A, 11B, 11C:
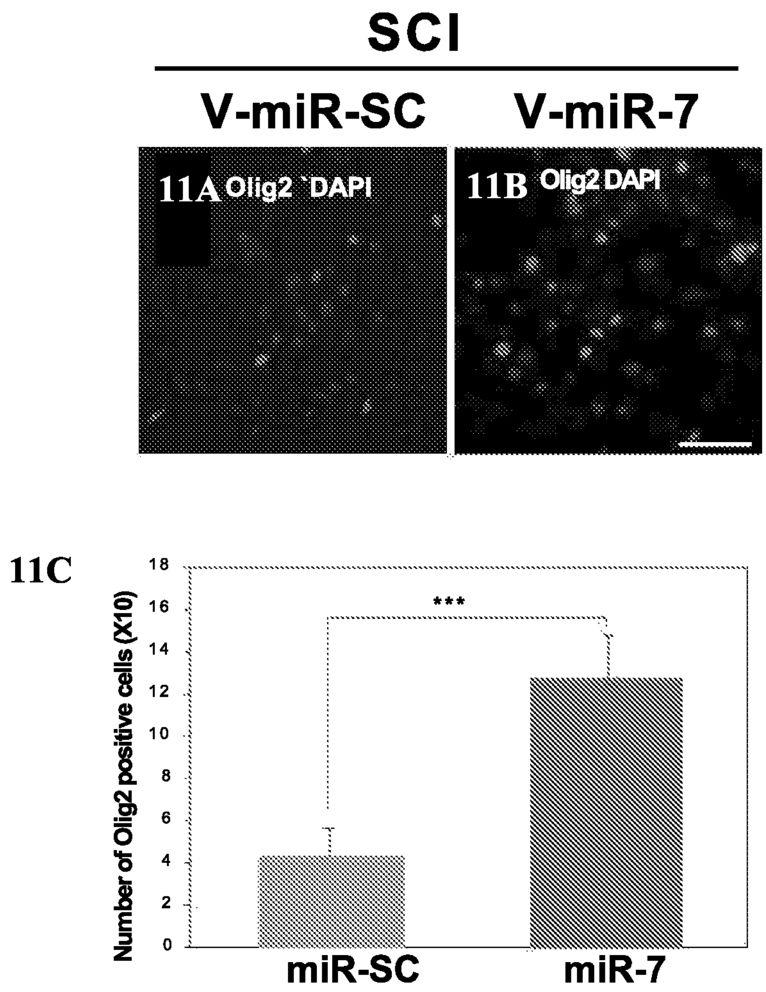
FIGS. 11A, 11B and 11C are a pair of fluorescence images and a graph showing increased survival of oligodendrocytes by AAV1-miR-7 transduction at 4 weeks post-injury. Representative images of sagittal sections stained with Olig2 antibody (oligodendrocyte marker, 1:300, cat#AB9610, Chemicon, Bedford, MA) are shown. Numbers of Olig2-positive cells were counted from 5 randomly selected microscopic fields near injury center (FIG. 11C). Arrows indicate Olig2-positive cells. Bars indicate 50 μm. ***p<0.001 assessed by t-test. Data represent means±SEM, (n=4 mice).

Protection of oligodendrocytes. The death of oligodendrocytes producing myelin in the lesion causes axons to lose their myelination, which significantly impairs the relay of messages. Thus, the sparing of oligodendrocytes in the epicenter of the injury region was assessed. Sagittal sections stained with Olig2, a maker for oligodendrocyte showed an increased number of oligodendrocytes in AAV1-miR-7 injected mice at 4 weeks after injury (FIGS. 11A-11C). This result suggests that miR-7 protects oligodendrocytes from SCI-induced death.

Example 2—Treatment of SCI

A SCI is damage to the spinal cord, which causes permanent changes in strength, sensation and other body functions below the site of the injury. The first mechanical damage initiates a complex set of secondary molecular events that largely determine the symptoms of the SCI. Diverse cellular mechanisms responsible for this secondary injury mostly depend on changes of specific gene programs.

Previously it was shown that miR-7 exhibits a protective role in the cellular models of oxidative stress. In particular, miR-7 accomplishes neuroprotection by improving the health of mitochondria, a powerhouse in the cells. Mitochondrial activity is severely compromised following SCI, thus improving mitochondrial health could have therapeutic value for the treatment of spinal cord injury. Whether miR-7 promotes the functional recovery from SCI using a mouse model is investigated. miR-7 is delivered to injury sites using a viral vector and a gold nanoparticle, and its effect on locomotor behavior and cellular responses is assessed at 6 weeks post-delivery. It is expected that miR-7 results in better motor functional recovery from the severe spinal cord compression, and that miR-7 can be developed as a potential therapeutic for spinal cord injury.

Mitochondrial dysfunction contributes to cell death following SCI. In particular, opening of mitochondrial permeability transition pore (mPTP) has been linked to cell death following SCI. Therefore, promoting mitochondrial health by limiting mPTP formation could have therapeutic value for the treatment of SCI. It was previously shown that overexpression of miR-7 protects cells against mitochondrial toxin exposure through promoting mitochondrial function by targeting the expression of voltage dependent anion channel 1 (VDAC1), a constituent of the mPTP. It is hypothesized that exogenous expression of miR-7 can promote functional recovery by increasing mitochondrial function following SCI. miR-7 is delivered to injury sites using two different methods, lentivirus-mediated and gold nanoparticle-mediated, and its effect on locomotor behavior and cellular response is assessed at 6 weeks post-delivery. The neuroprotective effects are investigated by measuring remyelination, suppression of glial scar formation and apoptosis. In addition, behavior assessments measuring locomotor activity are also monitored over the time course of 8 weeks in a mouse model of SCI. It is expected that miR-7 presents better motor functional recovery from the severe spinal cord compression, and that miR-7 can be developed as a potential therapeutic for spinal cord injury.

Through earlier studies, it was found that miR-7 inhibits the function of mPTP by targeting the 3'-UTR of VDAC1 mRNA, a constituent of the mPTP. Targeting of VDAC1 mRNA by miR-7 resulted in a decrease of VDAC1 mRNA and protein levels. Consequently, miR-7 prevents opening of mPTP following mitochondrial toxin (MPP+), thereby conferring neuroprotection. As disruption of mitochondrial potential and formation of the mPTP contribute to the pathophysiological changes following SCI, it is postulated that miR-7 can promote cell survival and functional recovery following SCI through increasing mitochondrial health.

One of the most attractive properties of miRs as potential therapeutic agents is their ability to target multiple genes, often within the context of a network, which makes them very effective in regulating distinct biological pathways relevant to normal and disease conditions. Through earlier studies, it was also found that miR-7 inhibits cyclophilin D (CyD) expression, another component of mPTP. Therefore, it is expected that miR-7 inhibits mPTP formation by targeting CyD in addition to VDAC1. miR-7 is believed to be a potent regulator of mPTP by targeting expression of two components in mPTP, which consists of three proteins. In addition, it was recently reported that miR-7 activates Nrf2 pathway by targeting Keap1 expression, which is an inhibitor of Nrf2. Nrf2, a member of the Cap 'n' Collar (CNC) basic leucine zipper transcription factor family, regulates the expression of antioxidant and phase II detoxifying genes to protect against ROS-induced toxicity. Further, genetic ablation of Nrf2 exacerbated the neurological deficit and inflammation after SCI in mice, which suggests that Nrf2 could provide cell survival and functional recovery after SCI. Thus, miR-7 could promote functional recovery after SCI through activating Nrf2 pathway as well. As such, miR-7 can be exploited to activate several protective pathways at the same time, which subsequently leads to an enhanced functional recovery after SCI.

There are several challenges to develop miR-based therapeutics. One of them is the biological instability of these compounds in biological fluids or tissues as unmodified oligonucleotides are rapidly degraded by cellular and serum nucleases. Another problem is the poor cellular uptake of oligonucleotides due to their size and negative charge, which could prevent them from crossing through cell membranes. Therefore, several approaches have been devised to overcome these obstacles.

Nanoparticles have been developed as gene delivery vehicles, which is promising since they provide improved oligonucleotide delivery and stability with minimal toxicity in animal models. In particular, gold nanoparticles have been employed for drug delivery due to their non-toxic, non-immunoreactive, and biocompatible characteristics. Gold nanoparticles can be used to deliver miR-7 into severe compressed spinal cord, and evaluated as a potential therapeutic drug treatment for spinal cord injury.

Because miR-7 regulates the expression of mitochondrial proteins, a proteomic analysis was performed to determine the miR-7 target profile. Human neuroblastoma cells, SH-SY5Y were transfected with miR-7 or a scrambled control, miR-SC. Changes in protein expression were quantified using an iTRAQ-based proteomic platform. As miRs mostly downregulate the expression of their target proteins, the focus was on the proteins that were significantly ($p<0.05$) decreased in the miR-7-transfected cells. Two-hundred and eighty-four proteins were found to be significantly downregulated with a fold change of <0.8 in the miR-7 transfected cells. To identify over-represented groups of proteins, gene ontology (GO) analysis was performed using database for annotation, visualization and integrated discovery (DAVID). Three of the top ten enriched GO terms were pertaining to the mitochondria, namely, mitochondrion, mitochondrial part and mitochondrial large ribosome. The 19 downregulated proteins belonged to the GO-term, mitochondrial part. Therefore, it was postulated that miR-7 regulates the expression of mitochondrial proteins and could play a crucial role in modulating mitochondrial function.

miR-7 modulates mitochondrial morphology. The proteomics analysis prompted investigation of the mitochondrial biology in response to miR-7. First, the mitochondrial morphology was observed. To this end, MPP+, which is well-known to induce mitochondrial fragmentation by blocking complex I activity of the mitochondrial electron transport chain, was used. MPP+treatment resulted in mitochondrial fragmentation and clumping in SH-SY5Y cells and primary mouse cortical neurons infected with lenti-miR-SC (scrambled control), while overexpression of miR-7 by transducing lenti-miR-7 significantly preserved an intact mitochondrial network even in response to MPP+.

miR-7 regulates mitochondrial membrane potential. Next, whether miR-7 affects mitochondrial membrane potential was investigated by using JC-1. JC-1 is a lipophilic, cationic dye that can selectively enter into mitochondria of healthy cells and forms J-aggregates with red fluorescence (emission 590 nm). Following exposure to cytotoxic stimuli like MPP+, mitochondria are depolarized. As a result, J-aggregates fail to form and JC-1 remains in the cytosol as a diffuse green staining (emission 529 nm). The ratio of red/green fluorescent intensity therefore indicates the polarization state of mitochondria, with healthy mitochondria having a higher red/green intensity ratio. Exposure to MPP+for 12 h leads to depolarization of mitochondria in SH-SY5Y cells, observed as an increase in green fluorescence and a decrease in red/green intensity ratio. However, overexpression of miR-7 prevented mitochondrial depolarization after MPP+ treatment as evidenced by a significant increase in red/green fluorescent intensity ratio compared to cells transfected with miR-SC.

miR-7 regulates function of mitochondrial permeability transition pore (PTP). Depolarization of the mitochondria in response to cytotoxic stimuli occurs due to opening of the mitochondrial PTP. As miR-7 significantly inhibited mitochondrial depolarization following MPP+treatment, whether miR-7 inhibits the opening of the mitochondrial PTP was investigated. For this, the mitochondrial and cytosolic fractions were isolated, followed by Western blot analysis to detect release of mitochondrial proteins through the mitochondrial PTP. Exposure to MPP+led to an increase in pro-apoptotic proteins, cytochrome c and apoptosis inducing factor (AIF) in the cytosolic fraction. However, overexpression of miR-7 attenuated the release of these proteins as evidenced by lower cytosolic levels of AIF and cytochrome c compared to miR-SC-transfected cells, suggesting that miR-7 inhibits the opening of mitochondrial PTP. TOM20 was used as a marker for mitochondrial fraction and β-tubulin was used as a marker for the cytosolic fraction. In addition, opening of mitochondrial PTP also increases the level of reactive oxygen species (ROS). We quantified intracellular ROS levels using 2',7'-dichlorofluorescein diacetate (DCF-DA), an ROS-sensor probe. SH-SY5Y cells transfected with miR-7 appeared to have a lower basal level of intracellular ROS. Treatment with MPP+ led to a dose-dependent increase in ROS generation. However, in cells overexpressing miR-7, this increase was abrogated and these cells showed significantly less intracellular ROS levels with all doses of MPP+ tested. Taken together, these results indicate that miR-7 regulates mitochondrial PTP function and prevents its opening.

miR-7 targets the mitochondrial PTP component protein, VDAC1. As the results demonstrated that miR-7 regulates function of the mitochondrial PTP, the proteomics data was reviewed to identify if any of the 19 'mitochondrial part' proteins that were significantly downregulated by miR-7 were associated with the PTP. Indeed, it was found that voltage dependent anion channel 1 (VDAC1) was downregulated with fold change of 0.8 in the proteomic data. VDAC1 is an integral protein of the mitochondrial outer membrane and forms the channel for the mitochondrial PTP. Overexpression of miR-7 reduced the level of VDAC1 protein by 55%, confirming the observation from the proteomic study. qPCR analysis was performed to determine whether overexpression of miR-7 resulted in degradation of VDAC1 mRNA as well. Certainly, miR-7 led to a 60% decrease in VDAC1 mRNA levels. Further, it was desired to determine whether endogenous miR-7 is responsible for regulation VDAC1 expression by transfecting SH-SY5Y cells with miR-7 inhibitor (anti-miR-7) or control inhibitor (anti-miR-SC). Inhibition of miR-7 dramatically increased VDAC1 protein levels, suggesting that endogenous miR-7 represses VDAC1 expression. To identify the potential miR-7 binding site in the VDAC1 3'-UTR, a prediction algorithm from TargetScan was performed. A potential miR-7 target site in the 3'-UTR of VDAC1 mRNA was found, which is conserved in the human, chimpanzee, rhesus, rat, and mouse. To investigate whether miR-7 directly targets the 3'-UTR of VDAC1, this 3'-UTR was inserted downstream of the firefly luciferase reporter gene. Co-expression of miR-7 along with VDAC1 3'-UTR luciferase reporter vector led to a significant decrease in luciferase activity compared to co-expression of this vector with miR-SC. Also, miR-7 significantly decreased luciferase activity from the VDAC1 3'-UTR construct, but had no effect on pGL4.51 construct devoid of VDAC1 3'-UTR. To further verify that the predicted miR-7 binding site on VDAC1 3'-UTR is essential for its function, this site was mutated and the luciferase reporter assay was performed. As expected, miR-7 was unable to suppress luciferase reporter expression from the mutated VDAC1 3'-UTR, confirming the authenticity of the predicted binding site. Therefore, it was concluded that miR-7 directly targets VDAC1 and reduces its expression even after exposure to MPP+.

Overexpression of VDAC1 abrogates the protective effect of miR-7 on cell death and mitochondrial function. To study whether miR-7-mediated decrease in VDAC1 expression underlies the cytoprotective effect of miR-7 against MPP+, SH-SY5Y cells were transfected with plasmid containing VDAC1 cDNA without its 3'-UTR (pcDNA3.1-VDAC1), along with pre-miR-7. This approach restores VDAC1 levels despite downregulation of endogenous VDAC1 by miR-7. Propidium idiodie (PI) staining was performed to determine cell death in SH-SY5Y transfected as indicated. It was observed that the proportion of PI-positive (dead) cells dramatically increases to 67% upon MPP+treatment, while overexpression of miR-7 decreases PI-positive cells to 18%. Notably, overexpression of VDAC1 partly abolished the protective effect of miR-7 against MPP+, as evidenced by an increase in PI-positive cells from 18% in miR-7 and pcDNA3.1 co-transfected cells to 55% in miR-7 and VDAC1 co-transfected cells after exposure to MPP+. This result demonstrates that the cytoprotective effect of miR-7 against MPP+in part requires the down-regulation of VDAC1 expression. Taken together, it was concluded that miR-7 regulates the function of mitochondrial PTP and protects against MPP+-induced cytotoxicity by targeting VDAC1.

miR-7 downregulates cyclophilin D expression: As miR-7 targets VDAC1 expression, whether other components of mPTP, ANT and cyclophilin D, can be targeted by miR-7 was investigated. A potential miR-7 target site in 3'-UTR of cyclophilin D was identified, but not ANT. Indeed, overexpression of miR-7 reduced the level of cyclophilin D protein by about 40%. Further, to determine whether endogenous miR-7 is responsible for regulation cyclophilin D expression, SH-SY5Y cells were transfected with miR-7 inhibitor (anti-miR-7). Inhibition of miR-7 dramatically increased cyclophilin D protein levels, suggesting that endogenous miR-7 represses cyclophilin D expression. These results suggest that miR-7 might target cyclophilin D expression through its 3'-UTR.

The effect of lentiviral-mediated delivery of miR-7 on functional recovery in a mouse SCI model was investigated. Viral gene delivery for SCI is considered as a promising approach for enhancing axonal regeneration and neuroprotection. Lentiviral vectors are efficient for transduction of a variety of cells, and reportedly have the most stable pattern of gene expression after in vivo delivery to spinal cord, compared to adenoviral and retroviral infection. Therefore, lentivirus expressing miR-7 (lenti-miR-7) is infected into a spinal cord mice model. A compression model is used because compression spares some spinal cord tissue depending on the severity, which is more pertinent to clinical conditions as the spinal cord is hardly completely transected in accidents. C57BL/6J female mice of 2-3 months old are used for this study. Mice are anesthetized by intraperitoneal injections of ketamine and xylazine. Laminectomy is performed at T9—T10 levels with mouse laminectomy forceps. A spinal cord compression injury is performed as reported previously, which is easy and reproducible. This surgical SCI model is generated using a pair of calibrated No. 5 Dumont forceps modified to be held apart at a defined distance by 0.35 mm spacer to prevent complete closure. This spacer ensures that the forceps will always close to a certain width in multiple surgeries and by different users. The spinal cord is severely compressed to press the forceps to the spacer contact and held for 15 sec. Right after compression, one microliter of lenti-miR-7 or lenti-miR-SC (scrambled sequence control) having $1\times10^{8}$/ml viral titer is injected to the injury center, 2 mm rostral and caudal from the center of injured spinal cord at a depth of 1 mm using a stereotactically driven Hamilton syringe for 5 min. The skin is sutured using 6-0 nylon stitches. After the operation, mice are kept on a heated pad (35-37° C.) overnight to prevent hypothermia and thereafter singly housed. During the post-operative period, the bladders of the animals are manually voided twice daily, and mouse health (weight) are closely monitored. This study consists of 3 groups (lenti-miR-7, lenti-miR-SC and non-injured control) and each group of mice comprises 8 mice and is sacrificed 6 weeks after injury. This group size provides 84% power to detect a 25% difference (effect size 1.59) in the locomotor functions in lenti-miR7-infected samples compared to lenti-miR-SC (t-test, a set at 0.05). The results are expressed as means±SEM. The statistical significance of the differences with absolute values are assessed by t-test. The differences are considered statistically significant at p-values less than 5%. The experiment is repeated once. Thus, a total of 48 mice are used for this particular experiment.

To evaluate whether miR-7 overexpression can improve motor behavior after SCI, a set of motor function assays are performed, including the BMS, foot-stepping angle and ladder climbing. This testing is performed every week for 6 weeks post injury.

The BMS is used for evaluating locomotor function after SCI, which is a widely accepted test for assessing recovery of motor function after SCI. The scale ranges from 0 to 9, with 0 denoting complete hind limb paralysis and 9 representing normal locomotion. BMS 2-3 is usually shown in mice at 3-4 weeks after severe compression injury without any treatment. Scores are evaluated for left and right hind limbs and the average is calculated. The testing is performed by two researchers, one is a trained and the other is a blinded researcher.

To perform foot stepping angel, the mice are trained to walk on a wood beam (5 cm wide 100 cm long) every other day for 1 week before surgery. Video-tracking left and right side view of each animal is made during two consecutive walks on a wooden beam every other week. The leg angle is analyzed with base line using the affiliated analysis software (SIMI Motion; SIMI Reality Motion Systems, Unterschleissheim, Germany). The angle of foot and base from wild mice is about 20-30 degree but the angle become 160-170 when hind limb paralyzes completely.

To perform inclined ladder climbing to evaluate the hind-paw function, the mice are trained to climb a wood ladder (1 m long, parallel 10 cm apart, 100 rungs, 2 mm in diameter, 55 degree angle) every other day for 1 week before surgery. Mice are tested to cross the ladder 3 consecutive times, resting 25 seconds between each trial. Video is recorded at the end of training day before injury to obtain base line and the total number of grips from the hind paw are analyzed.

Biochemical and immunohistological analyses are employed to investigate the cellular response after SCI. The animals are sacrificed 6 weeks post SCI, to assess the following outcome measures:

Transduction efficiency is checked by examining GFP-positive cells in injected sites. To monitor miR-7 expression easily in the mouse spinal cord, Internal Ribosome Entry Sequence (IRES)-GFP expression unit were inserted downstream of miR-7 cDNA, thereby miR-7 and GFP are expressed bicistronically from a single mRNA in injured spinal cord. For this, animals are transcardially perfused with fresh 4% paraformaldehyde, and fixed spinal cord tissue will be cryoprotected in 30% sucrose, and sectioned into 20-pm-thick serial sagittal sections rostral and caudal to the lesion site, mounted on Superfrost Plus slides (Fisher Scientific). Sections are examined with fluorescence microscopy.

If the transduced GFP-positive cells express high-level of miR-7 is determined by in situ hybridization. Because GFP and miR-7 are produced from a single transcript bicistronically, it is expected that there will be a high level of miR-7 expression in GFP-positive cells.

The level of miR-7 target proteins including VDAC1 and Cyclophilin D is assessed in GFP-positive cells. It is expected there will be decreased expression of target proteins in GFP-positive cells due to the effect of over-expressed miR-7. Immunohistochemistry with an antibody to VDAC1 or Cyclophilin D is performed to visualize these proteins as red fluorescence. Expression levels are compared between lenti-miR-7 and lenti-SC injected animals. Also, the level of miR-7 targets are assessed using Western blot analysis using 5 mm injured area of spinal cord.

To assess mitochondrial health, mitochondrial fragmentation is measured in GFP-positive cells. For this, sections are stained with an antibody against TOM20 (mitochondrial marker protein), and it is expected that there will be less mitochondrial fragmentation in lenti-miR-7 infected animals.

As the neuroprotective function of miR-7 is expected, if lenti-miR-7 could rescue motor neurons in the caudal to the lesion site is investigated. Transverse sections are stained for choline acetyl transferase (ChAT), which is expressed in spinal motor neuronal cell bodies and in cholinergic boutons innervating the motor neurons. As a decrease in neuronal apoptosis in lenti-miR-7-injected mice is expected, neuronal apoptosis is investigated using TUNEL staining in rostral and caudal to injury epicenter (In Situ Cell Death Detection kit, Roche).

The glial scar acts like a physical barrier, so as to prevent axons to grow through it. Formation of glial scar is due to the inflammatory responses in the lesion. In addition to a protective role for motor neurons via the suggested mechanism, it is hypothesized that miR-7 can decrease the glial scar volume after SCI, based on a previous report to show the inhibitory effect on inflammatory response in vitro. Serial sagittal sections are stained with Cresyl violet/Luxol fast blue and used for estimations of the scar volume. GFAP immunostaining is also used for scar volume estimation, which are measured directly under the microscope using the StereoInvestigator software.

Following SCI there is a disruption of descending serotonergic projections to spinal motor areas, which results in a subsequent depletion in serotonin (5-HT). These changes in the serotonergic system can produce varying degrees of locomotor dysfunction through to paralysis. Using transverse sections, whether lenti-miR-7 transduction mitigates SCI-induced reduction in 5-HT immunoreactivity in axons caudal to injury site is investigated. The number of 5-HT-positive axons (shown as fibers) and the intensity of 5-HT staining is measured. As overexpression of miR-7 was previously shown to provide the longer neurites in mouse primary neurons challenged with mitochondrial toxin, it is postulated that miR-7 enhances axonal sparing and regrowth. Thus, it is expected that a significant increase will be observed in the number/intensity of immunoreactive fibers in the lenti-miR-7 as compared to the lenti-miR-SC control group.

The death of oligodendrocytes producing myelin in the lesion causes axons to lose their myelination, which significantly impairs the relay of messages, and thus renders the remaining connections useless. It is postulated that increased mitochondrial health provided by miR-7 can also protect oligodendrocyte death following SCI. In addition, it was previously reported that miR-7 promotes oligodendrogenesis from neural progenitor cells (NPC) in vitro. Therefore, it is speculated that overexpression of miR-7 in the lesion leads to an increase in axon remyelination possibly through protecting oligodendrocyte death and (or) effective generation of oligodendrocytes from NPC. For this, white matter sparing is measured using eriochrome cyanin R, which can stain preserved myelin blue with serial sagittal sections. The amount of myelin stained is quantitated using ImageJ and expressed as a percentage of the total area of the section.

Nanoparticles have gained interest as drug delivery systems due to localized and sustained release as well as a promising risk-to-benefit ratio. Nanoparticles such as chitosan, magnetic ion, glycolic/lactic acid polymer have been employed in SCI. Further, gold nanoparticles (AuNPs) are promising candidates for drug delivery due to their inert and nonimmunogenic characteristics, biocompatibility, easy preparation and modification. Especially, a PEG coating has been applied to increase colloidal stability of AuNPs, enhance their solubility and pharmacokinetic properties, and reduce toxicity. It was recently reported that PEG-functionalized 40-nm-AuNP is beneficial for mouse spinal cord injury (Papastefanaki et al., Mol Ther 23:993-1002, 2015). In the experiment described below, pre-miR-7 is mixed with PEG-AuNP.

For the preparation of pre-miR-7-PEG-AuNPs,_PEG-AuNP (40 nm) is purchased from Nanohybrid, and pre-miR-7 from Ambion. Pre-miR-7 is mixed with PEG-AuNPs at three different ratios (PEG-AuNPs:pre-miR-7=250 ng:50 pmole, 500 ng:50 pmole, 750 ng:50 pmole in DECP treated phosphate-buffered saline (PBS) solution for 1 hr at room temperature. Complex of pre-miR-7-AuNPs (nanoplex) is formed by electrostatic interaction between anionic pre-miR-7 and positive PEG-AuNP. This is followed by centrifugation (20,000 g, 30 min, 4° C.) to remove supernatant for unbounded pre-miR-7, and resuspension of the pellet in PBS. To evaluate the binding efficiency among 3 different ratios, the reaction mixture (15 μleach sample) is saved before spin down, and analyzed in the 2% agarose gel electrophoresis. The successful nanoplex appears as higher molecular weight bands compared with unbound pre-miR-7. The best ratio (PEG-AuNPs:pre-miR-7) to form nanoplex is determined.

For testing of pre-miR-7-AuNPs in vitro, the ability to be taken up by the cells is tested using human neuroblatoma cells, SH-SY5Y and mouse primary neurons. As miR-7 was previously shown to be protective against MPP+-induced cell death, whether this nanoplex exhibits cell protection against MPP+ is assessed using a cell survival assay kit (Promega). In addition, whether known targets of miR-7 such as VDAC1, Keap1 and RelA are successfully down-regulated by these nanoplexes is investigated using Western blot analysis.

For injection of pre-miR-7-AuNPs into SCI mice, right after compression, one microliter of nanoplex (1 nmole) is injected to the injury center, 2 mm rostral and caudal from the center of injured spinal cord at a depth of 1 mm using a stereotactically driven Hamilton syringe for 5 min. The effect of nanoplex at 6 weeks post injection is analyzed as described above. This study consists of 3 groups (pre-miR-7, pre-miR-SC and non-injured control) and each group of mice comprises 8 mice. This experiment is repeated once. Thus, a total of 48 mice are used.

Other Embodiments

All nucleic acids, nucleic acid names, genes, gene names, and gene products disclosed herein are intended to correspond to homologs from any species for which the compositions, viruses, vectors, nanoparticles, kits, and methods disclosed herein are applicable. Thus, the terms include, but are not limited to, nucleic acids, genes and gene products from humans, mice, dogs, etc. It is understood that when a nucleic acid, gene or gene product from a particular species is disclosed, this disclosure is intended to be exemplary only, and is not to be interpreted as a limitation unless the context in which it appears clearly indicates. Any improvement may be made in part or all of the compositions, viruses, vectors, nanoparticles, kits, and method steps. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method of treating a spinal cord injury (SCI) in a subject comprising administering to the subject having an SCI an effective amount of a recombinant virus to promote functional recovery in the subject by inducing neuronal survival and axon regeneration, a recombinant viral vector comprising a polynucleotide sequence comprising a nucleic acid sequence encoding pre-miR-7, or an effective amount of a composition comprising the recombinant virus comprising a recombinant viral vector comprising a polynucleotide sequence comprising a nucleic acid sequence encoding pre-miR-7, wherein the recombinant virus vector is a rAAV comprising serotype 1 or 9 capsid proteins and the rAAV vector is a serotype 2 rAAV vector.

2. The method of claim 1, wherein the subject is a mammal.

3. The method of claim 2, wherein the mammal is a human.

4. The method of claim 1, wherein administration of the recombinant virus or the composition comprising the recombinant virus improves at least one of: locomotor function, bladder function, bowel function, numbness and tingling in the subject.

5. The method of claim 1, wherein the recombinant virus or the composition comprising the recombinant virus is administered directly to the subject's spinal cord.

6. The method of claim 1, wherein the recombinant virus or the composition comprising the recombinant virus is administered to the subject at least one timepoint selected from the group consisting of: within one hour of SCI injury, within 2 hours of SCI injury, within 4 hours of SCI injury, within 6 hours of SCI injury, within 8 hours of SCI injury, within 12 hours of SCI injury, within 24 hours of SCI injury, within 48 hours of SCI injury, within 72 hours of SCI injury, within 7 days of SCI injury, and within one month of SCI injury.

7. The method of claim 1, wherein the subject is administered the recombinant virus or the composition comprising the recombinant virus via injection.

8. The method of claim 4, further comprising conducting assays for measuring improvement of at least one of locomotor function, bladder function, bowel function, numbness and tingling in the subject at a time point subsequent to administration of the recombinant virus or the composition comprising the recombinant virus.

* * * * *

SEQUENCE LISTING

```
<160> NUMBER OF SEQ ID NOS: 1

<210> SEQ ID NO 1
<211> LENGTH: 110
<212> TYPE: RNA
<213> ORGANISM: HOMO SAPIENS

<400> SEQUENCE: 1

uuggauguug gccuaguucu guguggaaga cuagugauuu uguuguuuuu agauaacuaa      60

aucgacaaca aaucacaguc ugccauaugg cacaggccau gccucuacag                110
```